United States Patent [19]
Yabe et al.

[11] Patent Number: 5,697,887
[45] Date of Patent: Dec. 16, 1997

[54] ENDOSCOPE COVER APPARATUS FOR USE WITH COVER-TYPE ENDOSCOPE AND ENDOSCOPE COVER HOLDING APPARATUS

[75] Inventors: Hisao Yabe, Hachioji; Yoshio Tashiro, Hino; Yoshihiro Iida, Tama; Akira Suzuki, Hachioji; Hideo Itoh, Hachioji; Minoru Yamazaki, Hachioji; Osamu Tamada, Hachioji; Yasuhito Kura, Hachioji, all of Japan

[73] Assignee: Olympus Optical Co., Ltd., Tokyo, Japan

[21] Appl. No.: 38,840

[22] Filed: Mar. 29, 1993

[30] Foreign Application Priority Data

| Feb. 23, 1993 | [JP] | Japan | UMH5-006271 |
| Feb. 23, 1993 | [JP] | Japan | UMH5-006272 |
| Feb. 23, 1993 | [JP] | Japan | UMH5-006273 |

[51] Int. Cl.[6] ................................ A61B 1/04
[52] U.S. Cl. ........................... 600/123; 600/121
[58] Field of Search ............... 128/4, 6; 600/121, 600/122, 123, 124, 125

[56] References Cited

U.S. PATENT DOCUMENTS

| Re. 34,110 | 10/1992 | Opie . | |
| 3,162,190 | 12/1964 | Del Gizzo . | |
| 4,646,722 | 3/1987 | Silverstein | 128/4 |
| 4,721,097 | 1/1988 | D'Amelio | 128/4 |
| 4,741,326 | 5/1988 | Sidall | 128/4 |
| 4,825,850 | 5/1989 | Opie | 128/4 |
| 4,869,238 | 9/1989 | Opie | 128/6 |
| 4,886,049 | 12/1989 | Darras | 128/4 |
| 4,907,395 | 3/1990 | Opie et al. . | |
| 4,991,564 | 2/1991 | Takahashi et al. . | |
| 4,991,565 | 2/1991 | Takahashi et al. . | |
| 4,997,084 | 3/1991 | Opie et al. . | |
| 5,050,585 | 9/1991 | Takahashi | 128/4 |
| 5,058,567 | 10/1991 | Takahashi | 128/4 |
| 5,105,800 | 4/1992 | Takahashi et al. . | |
| 5,201,908 | 4/1993 | Jones | 128/4 |
| 5,419,310 | 5/1995 | Frassila et al. | 600/121 |

FOREIGN PATENT DOCUMENTS

| 0 184 778 | 6/1986 | European Pat. Off. . |
| 0 310 515 | 4/1989 | European Pat. Off. . |
| 0 338 567 | 10/1989 | European Pat. Off. . |
| 0 341 718 | 11/1989 | European Pat. Off. . |
| 0 341 719 | 11/1989 | European Pat. Off. . |
| 0 349 479 | 1/1990 | European Pat. Off. . |
| 0 440 252 | 8/1991 | European Pat. Off. . |
| 0 440 254 | 8/1991 | European Pat. Off. . |
| 0 444 429 | 9/1991 | European Pat. Off. . |
| 39 09 290 | 10/1989 | Germany . |
| 51-47587 | 4/1976 | Japan . |
| 51-103891 | 8/1976 | Japan . |
| 52-95284 | 7/1977 | Japan . |
| 58-44033 | 3/1983 | Japan . |
| 62-177701 | 11/1987 | Japan . |
| 1-140902 | 9/1989 | Japan . |
| 2-57228 | 2/1990 | Japan . |
| 2-54734 | 11/1990 | Japan . |
| 3-13105 | 2/1991 | Japan . |
| 3-29634 | 2/1991 | Japan . |
| 3-29635 | 2/1991 | Japan . |

(List continued on next page.)

*Primary Examiner*—Beverly M. Flanagan
*Attorney, Agent, or Firm*—Armstrong, Westerman, Hattori, McLeland & Naughton

[57] ABSTRACT

An endoscope cover apparatus including a joint portion for fixing a control portion of an endoscope disposed adjacent to an operator, and extending insertion-portion cover disposed in front of the joint portion, a cover leading member disposed in the leading portion of the insertion-portion cover, a first tubular passage member passing through the cover-type endoscope from the joint portion to the cover leading member to continuously connect opening portions respectively formed in the cover leading member and the joint portion, and a second tubular passage member for continuously connecting the tubular passage of the joint portion to an external device.

14 Claims, 23 Drawing Sheets

FOREIGN PATENT DOCUMENTS

| | | |
|---|---|---|
| 3-37029 | 2/1991 | Japan . |
| 3-37030 | 2/1991 | Japan . |
| 3-221024 | 9/1991 | Japan . |
| 3-101901 | 10/1991 | Japan . |
| 3-101902 | 10/1991 | Japan . |
| 3-101903 | 10/1991 | Japan . |
| 3-101904 | 10/1991 | Japan . |
| 3-101905 | 10/1991 | Japan . |
| 3-101906 | 10/1991 | Japan . |
| 3-101907 | 10/1991 | Japan . |
| H4-325138 | 11/1992 | Japan . |
| 5103756 | 4/1993 | Japan ............... 128/4 |

ENDOSCOPE COVER APPARATUS FOR USE WITH COVER-TYPE ENDOSCOPE AND ENDOSCOPE COVER HOLDING APPARATUS

BACKGROUND OF THE INVENTION

1. Field of the Invention

The present invention relates to an endoscope cover apparatus for covering an endoscope and to an endoscope cover holding apparatus, and more particularly to an endoscope cover apparatus wherein, for example, a suction tubular passage and an air/water supply tubular passage respectively are divided into an insertion portion and an external device portion, and to an endoscope cover holding apparatus for use at the time of attaching/detaching an endoscope cover to and from a cover-type endoscope.

2. Description of the Related Art

Recently, an endoscope having an elongated insertion portion to be inserted into the body cavity to diagnose or cure a patient or the like has been widely used. When the inspection with the endoscope is performed, it is necessary to use a clean endoscope which has been previously and sufficiently cleaned and disinfected. Therefore, the endoscope contaminated from use in the body cavity of a patient is cleaned and disinfected by various methods prior to using the endoscope in the body cavity of the next patient. However, it usually takes a long time to completely clean the endoscope.

In order to overcome the foregoing problem, an endoscope adaptable to a disposable-type endoscope cover has been suggested in place of the endoscope for use with a conventional repeated-use-type endoscope cover.

The endoscope-cover-type endoscope comprises an endoscope cover for covering the outer surface of the insertion portion and so forth and an endoscope-cover-type endoscope to be inserted into the endoscope cover. An example of the endoscope-cover-type endoscope has been disclosed in, for example, U.S. Pat. No. 3,162,190.

The foregoing related art has been arranged to prevent contamination of the endoscope by covering the endoscope with an endoscope cover. It should be noted that an endoscope cover provided with a channel to be described later is hereinafter referred to as a channel-provided endoscope cover.

An endoscope of the (channel-provided) endoscope cover-type comprises a channel-provided endoscope cover (hereinafter called a "cover") and an endoscope-cover-type endoscope (hereinafter called a "cover-type endoscope cover"), the endoscope of this type having a structure in which the insertion portion and so forth of the cover-type endoscope can be covered with the foregoing cover. The endoscope of this type is inserted into the body cavity of a patient in a state where the cover-type endoscope is covered with the cover so that contamination of the cover-type endoscope is prevented. It should be noted that the disposable channel-provided endoscope cover is removed and disposed for example after use.

The insertion portion of the cover-type endoscope is provided with, for example, an image sensing system or an observation optical system and a light guide fiber.

Since a forceps-channel and air/water supply tube can be contaminated with body fluid or the like and cannot easily be cleaned and disinfected due to its elongated shape, the foregoing channel is integrally fastened to the channel-provided endoscope cover to be disposable. That is, tubes each having two open ends, such as a curing tool channel and an air/water supply pipe, are provided for the channel-provided endoscope cover. By making the channel-provided endoscope to be disposable for each patient, as described above, the necessity of cleaning and disinfecting the cover-type endoscope can be eliminated for a long time. Since the necessity of cleaning and disinfecting the cover-type endoscope can be eliminated for a long time, the endoscope inspection can be continuously performed for a plurality of patients.

FIG. 3 illustrates a cover 2A for covering a cover-type endoscope 2B, FIG. 3 being a cross sectional view which illustrates the cover 2A to which the cover-type endoscope 2B is fastened.

When an inspection with the endoscope is performed, the clean cover-type endoscope 2B is covered with the clean cover 2A. After the inspection has been completed, the cover 2A is disposed, for example. On the other hand, the cover-type endoscope 2B is covered with a new cover 2A so that the cover-type endoscope 2B is used repeatedly.

As shown in FIG. 3, the cover 2A for covering the cover-type endoscope 2B comprises an insertion-portion cover 11A for covering an insertion portion 11B of the cover-type endoscope 2B, a control-portion cover for covering a control portion (omitted from illustration) of the cover-type endoscope 2B, and a universal-cord cover (omitted from illustration) for covering a universal cord of the cover-type endoscope 2B.

The insertion-portion cover 11A is formed into an elongated shape to correspond to the insertion portion 11B of the cover-type endoscope 2B. An endoscope control-portion fixing joint portion 18 (hereinafter abbreviated to a "fixing joint portion") disposed in a portion of the insertion-portion cover 11A adjacent to an operator and a cover leading portion 19A disposed in the leading portion, respectively, are made of hard material. The fixing joint portion 18 has an endoscope insertion channel 38 through which the insertion portion 11B of the cover-type endoscope 2B is inserted, an air/water supply tubular passage 27, and a suction tubular passage 29.

The cover leading portion 19A has a cover observation window 23A and a forceps-port outlet port 43 for connecting an air/water supply nozzle 31 to a forceps channel 35. The insertion-portion cover 11A has an endoscope insertion channel 38 through which the insertion portion 11B of the cover-type endoscope 2B is inserted, and a forceps channel 35 also serving as a suction tubular passage. The cover 2A thus arranged is formed by connecting the cover leading portion 19A, the insertion-portion cover 11A and the endoscope control-portion fixing joint portion 18.

The illustrated cover 2A has a suction tube 30 in which the suction tubular passage 29 forms the forceps channel 35 is formed into a sole tube which penetrates through the fixing joint portion from the portion adjacent to the external device, and passes through the insertion-portion cover 11A, followed by connection with the cover leading portion 19A. The foregoing cover 2A is arranged so that the air/water supply tube 28 is formed into a sole tube that penetrates the fixing joint portion from a portion adjacent to the external device. The air/water supply tube 28 further passes through the insertion portion cover 11A so that it is connected to the cover leading portion 19A.

The fixing joint portion 18 includes an expansion tube joint 37 to be connected to an expander for supplying air to the endoscope insertion channel 38 for the purpose of easily inserting the cover-type endoscope 2B, the fixing joint portion 18 further including a forceps insertion port 32 through which the forceps is inserted and which is connected to a forceps channel 35 in the suction tube 30.

The fixing joint portion 18 has a flange portion 18A on the outer periphery of an end portion thereof. The flange portion 18A is hooked and held by a semicircular holding portion provided for an endoscope cover holding apparatus (omitted from illustration) when, for example, the cover-type endoscope 2B is inserted (fastened) or removed from the endoscope cover 2A.

Furthermore, the fixing joint portion 18 has, in an end portion thereof, an opening 39 of an endoscope insertion channel 38 through which the insertion portion 11B of the cover-type endoscope 2B is inserted (fastened). The endoscope insertion channel 38 is connected to the expansion tube joint 37 formed so as to open on the side of the fixing joint portion 18.

The illustrated endoscope cover 2A comprises an expander connection tube to be connected to the expansion tube joint 37 which is connected to an expander, which is an external device.

A method for forming the cover 2A thus arranged to form the cover-type endoscope 2B will now be described with reference to FIG. 4.

FIG. 4 illustrates a method of manufacturing the cover 2A for covering the cover-type endoscope 2B.

First, the leading portions of the suction tube 30 and the air/water supply tube 28, respectively, are connected to the cover leading portion 19A. The insertion-portion cover 11A having a predetermined length is inserted from the portion adjacent to the leading portions of the suction tube and the air/water supply tube 28. The leading portion of the insertion-portion cover 19A is connected to the cover leading portion 19A.

Then, the fixing joint portion 18 is, as shown in FIG. 4, inserted at a position adjacent to the base portions of the suction tube 30 and the air/water supply tube 28. In this case, the suction tube 30 and the air/water supply tube 28 are inserted into a through-hole formed in the fixing joint portion 18. The inserted fixing joint portion 18 is shifted to the trailing end (in a direction designated by an arrow of FIG. 4) of the insertion-portion cover 11A along the suction tube 30 and the air/water supply tube 28. The operation of shifting the fixing joint portion 18 is continued until it reaches the base portion of the insertion-portion cover 11A. Then, the leading portion of the fixing joint portion 18 and the base portion of the insertion-portion cover 11A are connected to each other.

Finally, a hole is formed in the suction tube 29 so that the forceps tubular passage 33 of the fixing joint portion 18 positioned and connected as described above and the suction tube 29 are connected to each other. As a result, a forceps insertion branching portion 34 is created, and thus the endoscope cover 2A is formed.

The foregoing forming method encounters a fear of twisting or undesirable bending when the suction tube 30 and the air/water supply tube 28 is fastened to the fixing joint portion 18. Therefore, considerable attention must be paid at the time of this work and a difficulty arises in this work.

Furthermore, the fact that the forceps insertion portion branching portion 34 shown in FIG. 3 is formed after the insertion-portion cover 11A and the fixing joint portion 18 are fastened to each other raises a necessity of forming the through-hole in the suction tube 30 so as to establish the connection with the forceps insertion port 32. Moreover, the contamination in the insertion-portion cover 11A must be prevented by hermetically sealing the suction tube 30, the fixing joint portion 18 and the forceps insertion port 32. The foregoing work is not easy to perform. What is worse, the cover leading portion 19A and the fixing joint portion 18 are not mechanically fixed, resulting in difficulty in locating them.

Then, an operation when the endoscope cover 2A is used at the time of performing an endoscope inspection will now be described with reference to FIG. 3.

If the cover-type endoscope 2B is inserted (fastened) into the insertion-portion cover 11A of the endoscope cover 2A, the flange portion 18A of the fixing joint portion 18 is held by a semicircular holding portion provided for the endoscope cover holding apparatus (omitted from illustration). As a result, the insertion-portion cover 11A is fixed.

Then, an expansion connection tube (omitted from illustration) connected to the expander serving as the external device is connected to the expansion tube joint 37 provided for the fixing joint portion 18, followed by providing a supply of air to the endoscope insertion channel 8 from the cover expander, resulting in leakage of thus supplied air through the opening portion 39.

When the cover-type endoscope 2B is inserted into the opening portion 39, the opening portion 39 is substantially closed, causing air to expand an insertion-portion cover outer case 17A via the endoscope insertion channel 38. As a result, the endoscope insertion portion 11B can smoothly be inserted.

After the insertion work has been completed, the end portion of the expansion connection tube is removed from the expansion tube joint 37. Thus, air leaks through the expansion tube joint 37, causing the endoscope insertion channel 38 to be contracted due to its elasticity (the inner diameter of the endoscope insertion channel 38 is reduced). As a result, the outer surface of the endoscope insertion portion 11B, that is, the outer periphery of the insertion portion 11B is in substantially hermetic contact with the inner surface of the endoscope insertion channel 38.

Then, the control-portion cover and the insertion-portion cover 11A is, although omitted from illustration, connected by fastening a control-portion cover fitting portion 12C provided in the leading portion of the control-portion cover and the flange portion 18A provided for the fixing joint portion 18. Thus, the control-portion cover and the insertion-portion cover 11A are connected to each other so that the cover-type endoscope 2B is covered with the endoscope cover 2A.

Although omitted from illustration, the suction tube 30 and the air/water supply tube 28 projecting over the base portion of the fixing joint portion 18 pass through the control-portion cover, and are projected toward the external device together with the universal cord in a state in which they are covered with the universal cord cover. As a result, its base portion is connected to a fluid control device serving as an external device.

When the cover-type endoscope 2B is detached from the insertion-portion cover 11A after the endoscope inspection has been completed, a detaching tool (omitted from illustration) formed into the same shape as that of the foregoing cover holder is used to remove the cover-type endoscope 2B in the foregoing procedure.

Therefore, the expander connection tube is connected to the expansion tube joint 37 at the time of inserting (fastening) the cover-type endoscope 2B into the insertion-portion cover 11A. After the insertion has been made, the expander connection tube is separated from the expansion tube joint 37. Hence, the expander connection tube is a non-contaminated region at this time. However, there is a fear that the expansion tube joint 37 becomes a contaminated region because it is exposed to the outside during the inspection.

Since the expander connection tube, which is the non-contaminated region, is connected to the expander joint portion 37 to remove the cover-type endoscope 2B after the inspection has been completed, there is a possibility that also the expander connection tube becomes a contaminated region.

Accordingly, the expander connection tube must be sufficiently cleaned and disinfected at the time of use in order to continuously and safely perform the inspection.

Therefore, the arrangement of the endoscope cover apparatus shown in FIG. 3, in which the suction tube and the air/water supply tube are each formed by a single type tube, makes it necessary to insert the fixing joint portion from the base portions of the suction tube and the air/water supply tube to fasten the fixing joint portion. Moreover, the hole must be formed to pass the forceps insertion port and the suction tube after the fixing joint portion has been fastened. As a result, the contamination of the portion in the endoscope cover occurring from the hole portion must be prevented by hermetically sealing the forceps insertion portion in the fixing joint portion and the suction tube. Hence, the work for forming the endoscope cover is very complicated and difficult work. What is worse, there is a problem that the cover leading portion and the fixing joint portion cannot be easily located.

Since the expansion tube joint to be connected at the time of connecting/disconnecting the cover-type endoscope is exposed outside during the inspection, there is a possibility that the expansion tube joint becomes contaminated. In addition, there is a possibility that also the expander connection tube becomes a contaminated region, the expander connection tube serving to establish the connection between the expansion tube joint and the cover expander serving as the external device. In order to continuously and safely perform the inspections, the expander connection tube must be made disposable or it must be sufficiently cleaned and disinfected, which may take an excessive amount of time to accomplish.

If the outer surface of the insertion-portion cover or the base portion of the air/water supply tube or the suction tube touches the floor at the time of fastening the endoscope cover to the cover-type endoscope by using the endoscope cover holding apparatus, the endoscope cover can no longer be used.

SUMMARY OF THE INVENTION

An object of the present invention is to provide an endoscope cover apparatus which does require the need to form a hole for a suction tube when a fixing joint portion is fastened, with which the cover leading portion and the fixing joint portion can easily be located, and which facilitates assembling of the endoscope cover.

Another object of the present invention is to provide an endoscope cover apparatus with which continuous inspections can be safely performed, which eliminates the necessity of cleaning and disinfecting an expander connection tube, and which can be made disposable.

Another object of the present invention is to provide an endoscope cover holding device capable of preventing contamination due to contact of tubular passages such as an air/water supply tube and a suction tube and the like with a floor or the like in a case where a cover-type endoscope is inserted (fastened) to an endoscope cover, and which is capable of facilitating insertion and removal of the cover-type endoscope.

An endoscope cover apparatus according to the present invention comprises: a joint portion for fixing a control portion of an endoscope disposed adjacent to an operator; an extending insertion-portion cover disposed in front of the joint portion; a cover leading member disposed in the leading portion of the insertion-portion cover; a first tubular passage member passing through the cover-type endoscope from the joint portion to the cover leading member to continuously connect opening portions respectively formed in the cover leading member and the joint portion; and a second tubular passage member for continuously connecting the tubular passage of the joint portion to an external device.

Other and further objects, features and advantages of the invention will appear more fully from the following description.

BRIEF DESCRIPTION OF THE DRAWINGS

FIG. 1 is a cross sectional view which illustrates an endoscope cover apparatus;

FIG. 2 illustrates the overall shape of a cover-type endoscope apparatus which uses the endoscope cover apparatus shown in FIG. 1;

FIG. 5 is a cross sectional view which illustrates an endoscope cover apparatus;

FIG. 6 illustrates the overall shape of a cover-type-endoscope apparatus which uses the endoscope cover apparatus shown in FIG. 5;

FIG. 8 is a perspective view which illustrates the endoscope cover holding device;

FIG. 9 illustrates the overall shape of a cover-type endoscope apparatus which uses the endoscope cover holding device shown in FIG. 8;

DETAILED DESCRIPTION OF THE PREFERRED EMBODIMENTS

Preferred embodiments of the present invention will now be described with reference to the drawings.

Figure 1:
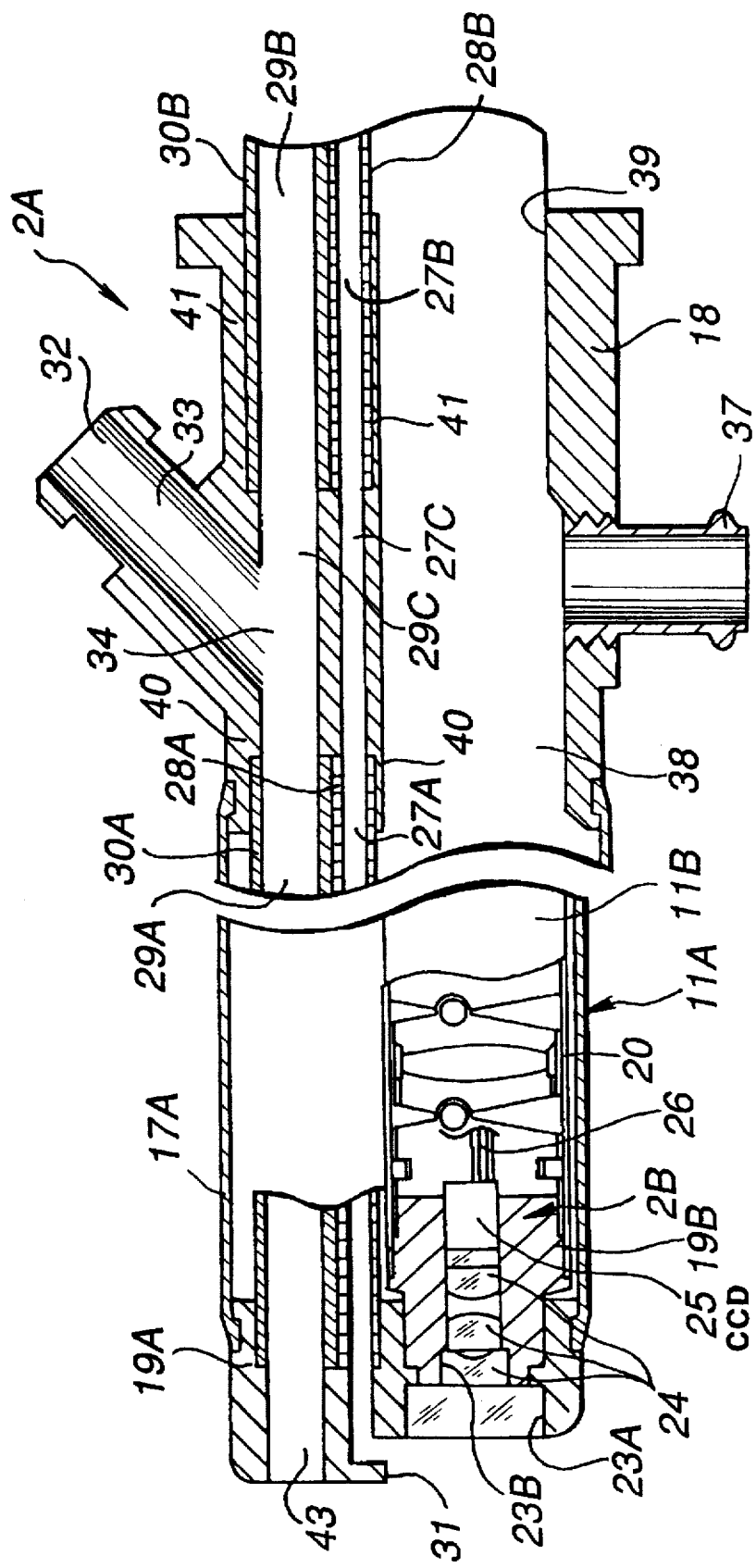
FIGS. 1 and 2 relate to a first embodiment of an endoscope cover apparatus according to the present invention, where
Figure 2:
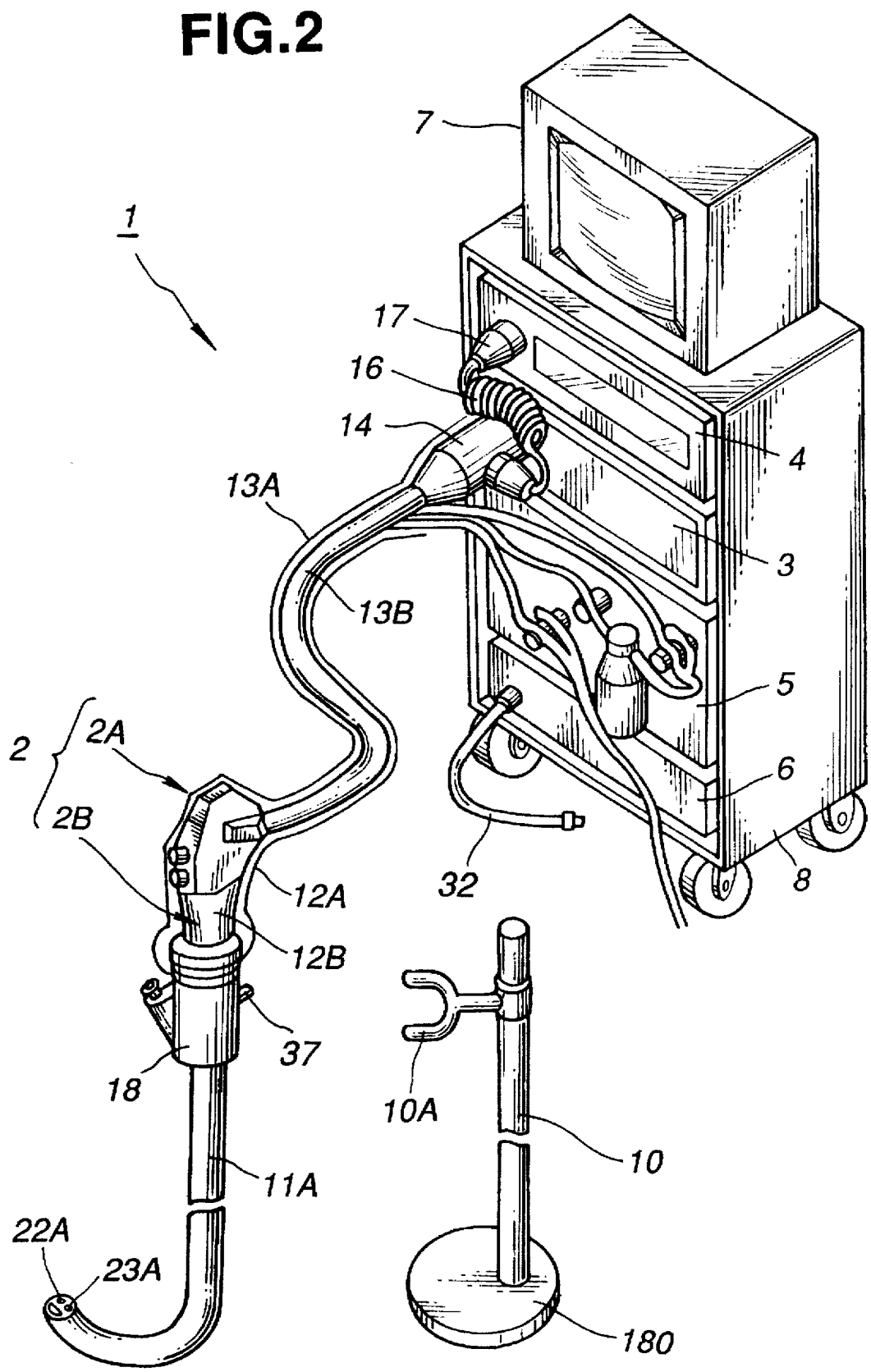

FIGS. 1 and 2 illustrate an embodiment of an endoscope cover apparatus according to the present invention. FIG. 1 is a cross sectional view which illustrates a state where a cover-type endoscope is fastened to the endoscope cover apparatus. FIG. 2 illustrates the overall shape of a channel-provided endoscope cover-type endoscope apparatus which uses the endoscope cover apparatus shown in FIG. 1.

An endoscope-cover-type endoscope apparatus (hereinafter called a "cover-type endoscope") 1 shown in FIG. 2 is an apparatus comprising a channel-provided endoscope-cover-type endoscope 2 (hereinafter abbreviated to a "cover-type endoscope").

The cover-type endoscope 2 is composed of a cover 2A for covering the endoscope and a cover-type endoscope 2B. The cover 2A covers an insertion portion 11B and so forth of the cover-type endoscope 2B to eliminate a necessity of cleaning and disinfecting the endoscope 2 after the inspection has been completed.

The endoscope apparatus 1 comprises the cover-type endoscope 2, a cart 8 including peripheral devices to which the cover-type endoscope 2 is connected, and a cover holder 10 for holding the cover-type endoscope 2.

As shown in FIG. 2, the cart 10 accommodating the peripheral devices accommodates, for example, a light source device 3, a video processor 4, a fluid control device 5, and a channel-provided endoscope cover expander 6 (hereinafter abbreviated to an "expander"). Furthermore, a monitor 7 is mounted on a ceiling plate of the cart 10.

The light source device 3 supplies irradiation light to the cover-type endoscope 2B of the cover-type endoscope 2. The video processor 4 is connected to the electronic cover-type endoscope 2B to convert an electric signal to a standard video signal to output the video signal to the monitor 7. The monitor 7 receives the video signal to display an endoscope image.

The fluid control device 5 supplies air/water through tubular passages to be described later, the tubular passages being disposed in the cover 2A. Therefore, the fluid control device 5 is provided with a water supply source and an air supply source (omitted from illustration). Furthermore, the tubular passages connected to the air supply source and the water supply source are opened and closed under the control of an electromagnetic valve to be opened/closed.

The expander 6 supplies air to the cover 2A to expand the cover 2A. The expansion enables the cover-type endoscope 2B to be easily attached/detached to and from the cover 2A.

FIG. 1 is an enlarged cross sectional view which illustrates a portion of the cover 2A of the cover-type endoscope 2 shown in FIG. 2. The cover 2A will now be described with reference to FIG. 2.

When an inspection with an endoscope is performed, the clean cover-type endoscope 2B is covered with a clean cover 2A. The cover 2A is disposed, for example, after the inspection has been completed, while the cover-type endoscope 2B is covered with a new and clean cover 2A to be repeatedly used.

When the cover-type endoscope 2B is fastened to an insertion-portion cover 11A constituting the cover 2A, or when the fastened cover-type endoscope 2B is detached, a cover holder 10 shown in FIG. 2 is used in such a manner that, for example, an endoscope insertion portion 11B of the cover-type endoscope 2B is inserted or removed in a state in which the base portion of the cover 2A is hooked to a semicircular holding portion 10A.

The cover-type endoscope 2B is composed of an endoscope insertion portion (hereinafter abbreviated to an "insertion portion") 11B formed into an elongated shape and having flexibility, an endoscope control portion (hereinafter abbreviated to a "control portion") 12B formed in the base portion of the insertion portion 11B, and a universal cord 13B extending from the side portion of the control portion 12B. A connector 14 disposed at the trailing end of the universal cord 13B can be detachably connected to the light source device 3. By establishing the connection with the light source device 3, irradiation light can be supplied to the end portion of a light guide (omitted from illustration) from a lamp included in the light source device 3.

The control portion 12B (see FIG. 2) has a warping knob on the side opposing the side from which the base portion of the universal cord 13B projects. By operating the warping knob, a warping portion 20 disposed in the leading portion of the insertion portion 11B can be warped. The control portion 12B has an air/water supply switch, a suction switch, and a freezing switch and the like. By operating the foregoing switches, air/water supply, suction and image freezing can be performed.

A cable 16 is extended from the connector 14, the cable 16 having a signal connector 17 disposed at the trailing end thereof and detachably connected to the video processor 4.

The cover 2A comprises the insertion portion 11B of the cover-type endoscope 2B, the insertion-portion cover 11A and a control-portion cover 12A for respectively covering the control portion 12B and the universal cord 13B, a control-portion 12A and a universal cord cover 13A.

The insertion-portion cover 11A is constituted by an insertion-portion cover outer case 17A for covering the insertion portion 11B, a fixing joint portion 18 hermetically disposed in the base portion of the insertion-portion cover outer case 17A and a cover leading portion 19A hermetically disposed in the base portion of the insertion-portion cover outer case 17A.

The cover 2A comprises the insertion-portion cover outer case 17A of the insertion-portion cover 11A, the control-portion cover 12A and the universal cord cover portion 13A made of synthetic resin such as polyurethane, polyester or silicon, for example.

Irradiation light supplied to an end surface of the light guide from a lamp (omitted from illustration) included in the light source device 3 is electrically transmitted through the light guide so that a forward subject is irradiated with the irradiation light through another end surface fastened to an irradiation window (omitted from illustration) of the leading portion 19B of the insertion portion 11B via a transparent plate of a cover irradiation window 22A (see FIG. 2) facing the foregoing end surface.

An optical image of the subject of a patient thus irradiated with the irradiation light is formed on the focal point surface of an object optical system 24 via a transparent plate of a cover observation window 23A formed adjacent to the cover irradiation window 22A and via the object optical system 24 fastened to an observation window 23B disposed inside the cover observation window 23A to face the same.

A CCD 25 is disposed on the foregoing focal point surface so that the optical image is photoelectrically converted, followed by receipt by the video processor via a signal cable (omitted from illustration) passing through the insertion portion 11B and the universal cord 13B and via the signal cable 16. The photoelectrically converted image is then processed so that a standard subject image is displayed.

As shown in FIG. 1, this embodiment of the present invention has an arrangement where the insertion-portion cover 11A includes the air/water supply tube 28A serving as a first tubular passage member, and a suction tube 30A serving as a tube for passing a forceps and a suction tube. The air/water supply tube 28A and the suction tube 30A respectively include a first air/water supply tubular passage 27A and a first suction tubular passage 29A. The leading portion of the first air/water supply tubular passage 27A is connected to a nozzle 31 of the cover leading portion 19A. The leading opening of the nozzle 31 faces the outer surface of the cover observation window 23A.

The base portions of the first air/water supply tubular passage tube 28A and the first suction tube 30A are connected to the fixing joint portion 18 by a joint leading-portion connection portion 40 disposed in the leading portion of the fixing joint portion 18.

The first air/water supply tube 28A and the first suction tube 30A are connected to a third air/water supply tubular passage 27C and a third suction tubular passage 29C formed in the fixing joint portion 18. Therefore, the first air/water supply tubular passage 27A is connected to the third air/water supply tubular passage 27C of the fixing joint portion 18 via a second air/water supply tubular passage 27B to be described later. The second air/water supply tube 28B including the second air/water supply tubular passage 27B is extended from the end portion of the fixing joint portion 18 toward an external device in such a manner that it is, together with a universal cord 13B, extended toward the fluid control device 5 while being covered with the universal cord cover portion 13A. As a result, the base portion of the second air/water supply tube 28B is connected to the fluid control device 5. Therefore, body fluid or the like adhered to the cover observation window 23A can be removed by supplying air or water via the air/water supply tubular passages 27B, 27C and 27A.

The fixing joint portion 18 has the air/water supply passage 27C and the suction tubular passage 29C as third tubular passages. The fixing joint portion 18 has a forceps insertion port 32 in the outer top surface thereof and has an expansion tube joint 37 for connecting an expansion tube 32 connected to an expander 6 on the outer lower surface thereof. The forceps insertion port 32 joins the third suction tubular passage 29C via a forceps insertion branching portion 34, followed by opening in a forceps port outlet port 43 also serving as a suction port in the cover leading portion 19A. As a result, a forceps and a curing tool inserted through the forceps insertion port 32 pass through a forceps tubular passage 33, the third suction tubular passage 29C and the first suction tubular passage 29A (a forceps channel), and projects over the forceps port 43.

In a portion more closely adjacent to an operator than the fixing joint portion 18, the second air/water supply tube 28B and the second suction tube 30B are disposed, the second air/water supply tube 28B and the second suction tube 30B being respectively connected to the air/water supply tubular passage 27C and the suction tubular passage 29C serving as the third tubular passages of the fixing joint portion 18. The second air/water supply tube 28B and the second suction tube 30B are connected to the fixing joint portion 18 by a joint bonding portion 41 adjacent to an operator. Therefore, the air/water supply tubular passage 27C and the suction tubular passage 29C serving as the third tubular passages respectively are connected to the second air/water supply tube 28B and the second suction tube 30B.

The fixing joint portion 18 has, in an end portion thereof, an opening portion 39 of an endoscope insertion channel 38 for inserting (fastening) the insertion portion 11B of the cover-type endoscope 2B. The endoscope insertion channel 38 is connected to the expansion tube joint 37 open on the side of the fixing joint portion 18. The endoscope insertion channel 38 corresponds to a space resulted by omitting the air/water supply tubular passages (27A to 27C) and the suction tubular passages (29A to 29C) from a space surrounded by the leading portion 19A, the insertion-portion cover outer case 17A and the fixing joint portion 18, the endoscope insertion channel 38 being a portion into which the cover-type endoscope 2B is inserted.

Then, a method of assembling the cover of the endoscope-cover-type endoscope thus constituted will now be described with reference to FIG. 1.

First, the cover leading portion 19A is connected to the leading portions of the first suction tube 30A and the first air/water supply tube 28A. In this case, the first suction tube 30A and the first air/water supply tube 28A have the same length and are formed into predetermined sizes respectively. The leading portion of the first suction tube 30A is inserted into the forceps output 43 formed in the cover leading portion 19A while being hermetically connected. Also the leading portion of the first air/water supply tube 28A is hermetically connected to the nozzle 31 disposed at the cover leading portion 19A.

Then, the base portions of the first suction tube 30A and the first air/water supply tube 28A are connected to the leading portion of the fixing joint portion 18. The fixing joint portion 18 has the previously formed forceps insertion branching portion 34, as shown in FIG. 2, and further includes the third tubular passages (29C and 27C). Therefore, the base portions of the first suction tube 30A and the first air/water supply tube 28A are hermetically connected by the joint leading-portion bonding portion 40 so as to be respectively connected to the third tubular passages, that is, the suction tubular passage 28C and the air/water supply tubular passage 27C.

Then, the insertion-portion cover 11A, the cover leading portion 19A and the fixing joint portion 18 are connected. The insertion-portion cover portion 11A has a predetermined length. The insertion-portion cover 11A is inserted from the cover leading portion 19A to cover the first suction tube 30A, the first air/water supply tube 28A and the endoscope insertion channel 38. Furthermore, the outer surface of the cover leading portion 19A and that of the fixing joint portion 18 are hermetically connected to each other.

Finally, the second suction tube 30B and the second air/water supply tube 28B are connected to a portion of the fixing joint portion 18 adjacent to an operator. In this case, the leading portions of the second suction tube 30B and the second air/water supply tube 28B are connected to the third tubular passages, that is, the suction tubular passage 29C and the air/water supply tubular passage 27C disposed in the portion of the fixing joint portion 18 adjacent to the operator. Thus, they are hermetically connected to the fixing joint portion 18 by the joint bonding portion 41 adjacent to an operator.

The second suction tube 30B and the second air/water supply tube 28B connected to the fixing joint portion 18 are, together with the universal cord 13B (see FIG. 2), extended while being covered with the universal cord cover 13A (see FIG. 2). As a result, their base portions are connected to the fluid control device 5.

Figure 3:
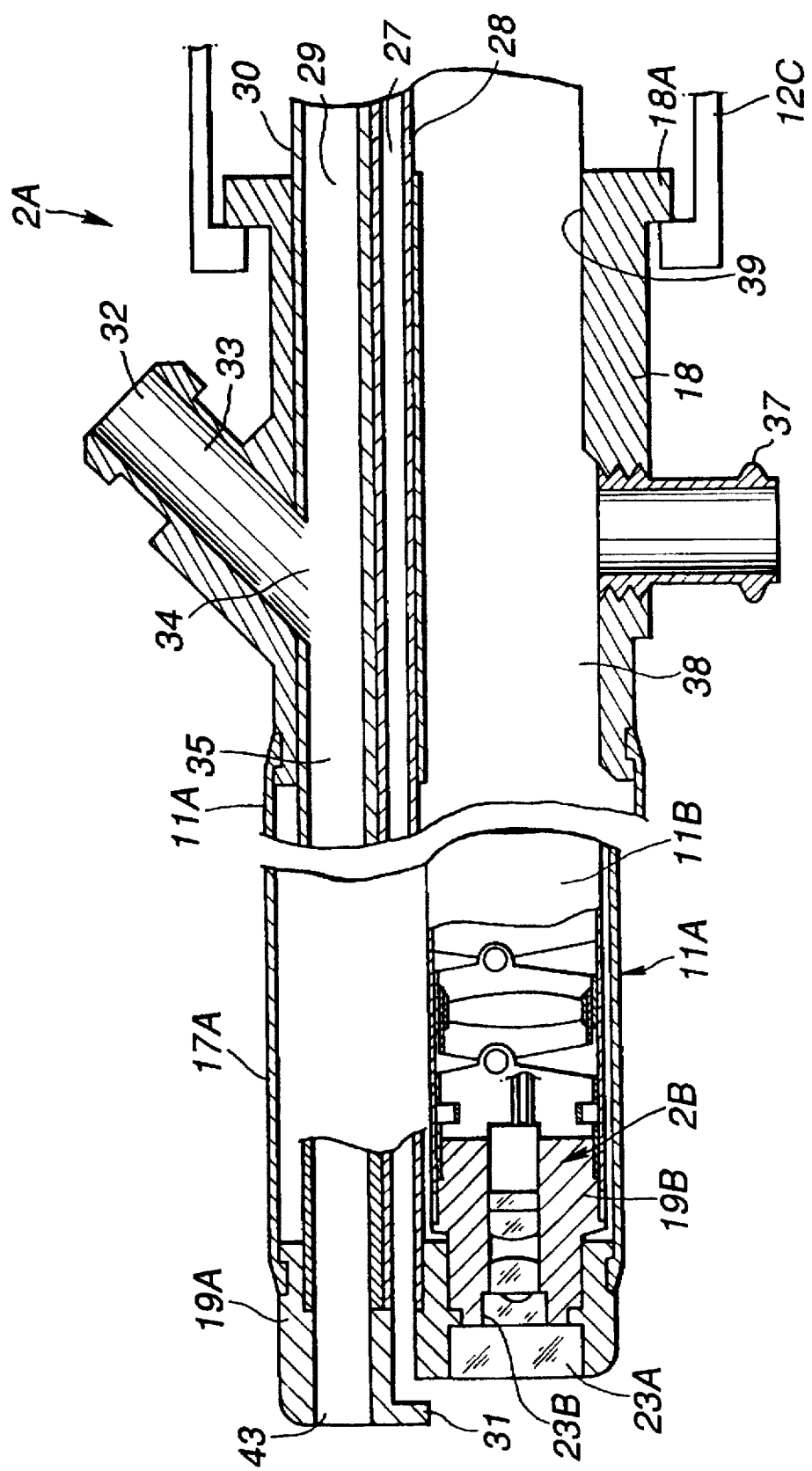
FIG. 3 is a cross sectional view which illustrates a channel-provided endoscope cover according to a related art.

Therefore, this embodiment is arranged such that the suction tube 30 and the air/water supply tube 28 of the endoscope cover 2A shown in FIG. 3 are formed individually. That is, the suction tube 30A and the air/water supply tube 28A, which are the first tubular members, and the suction tube 30B and the air/water supply tube 28B, which are the second tubular passage members, are provided.

Furthermore, the fixing joint portion 18 has the forceps insertion branching portion 34 therein. Furthermore, the third suction tubular passage 29C connected to the first and the second suction tubes 30A and 30B, and the third air/water supply tubular passage 27C connected to the first and the second air/water supply tubes 28A and 28B are formed.

Figure 4:
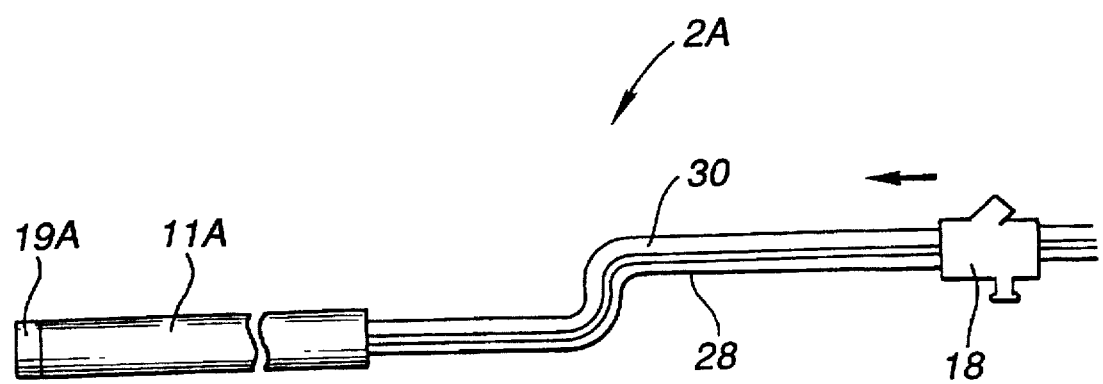
FIG. 4 illustrates a method of manufacturing the channel-provided endoscope cover shown in FIG. 3.

As a result, the work for assembling the endoscope cover 2A does not need a work of passing the fixing joint portion 18 into an elongated member as shown in FIG. 4, that is, a problem of twist or undesirable bending occurring at the time of assembling the cover 2A can be overcome. Therefore, the cover 2A can easily be assembled.

Since the fixing joint portion 18 according to the present invention has a previously formed forceps insertion branching portion 34, a work of forming a through-hole connected to the forceps tubular passage 33 and the suction tube 30 which has been required in the conventional technology can be omitted. Furthermore, a forceps or a curing tool can smoothly be inserted. Furthermore, the fact that the fixing joint portion 18 having the forceps insertion branching portion 34 is formed enables a sealing effect to be obtained, resulting in prevention of contamination of a portion in the insertion-portion cover 11A.

Since the first tubular passage member has a predetermined length, the cover leading portion 19A and the fixing joint portion 18 can easily be located.

As a result, the operation facility can be improved at the time of assembling the cover 2A of the cover-type endoscope.

Although the description of this embodiment is about the tubular passage members in the fixing joint portion 18, a connection port or the like may be formed which is opened in the outer surface of the fixing joint portion 18 and connected to the third tubular member and which has another function. The suction tube 30A may penetrate the forceps port outlet port 43 to extend to the end portion.

Figure 5:
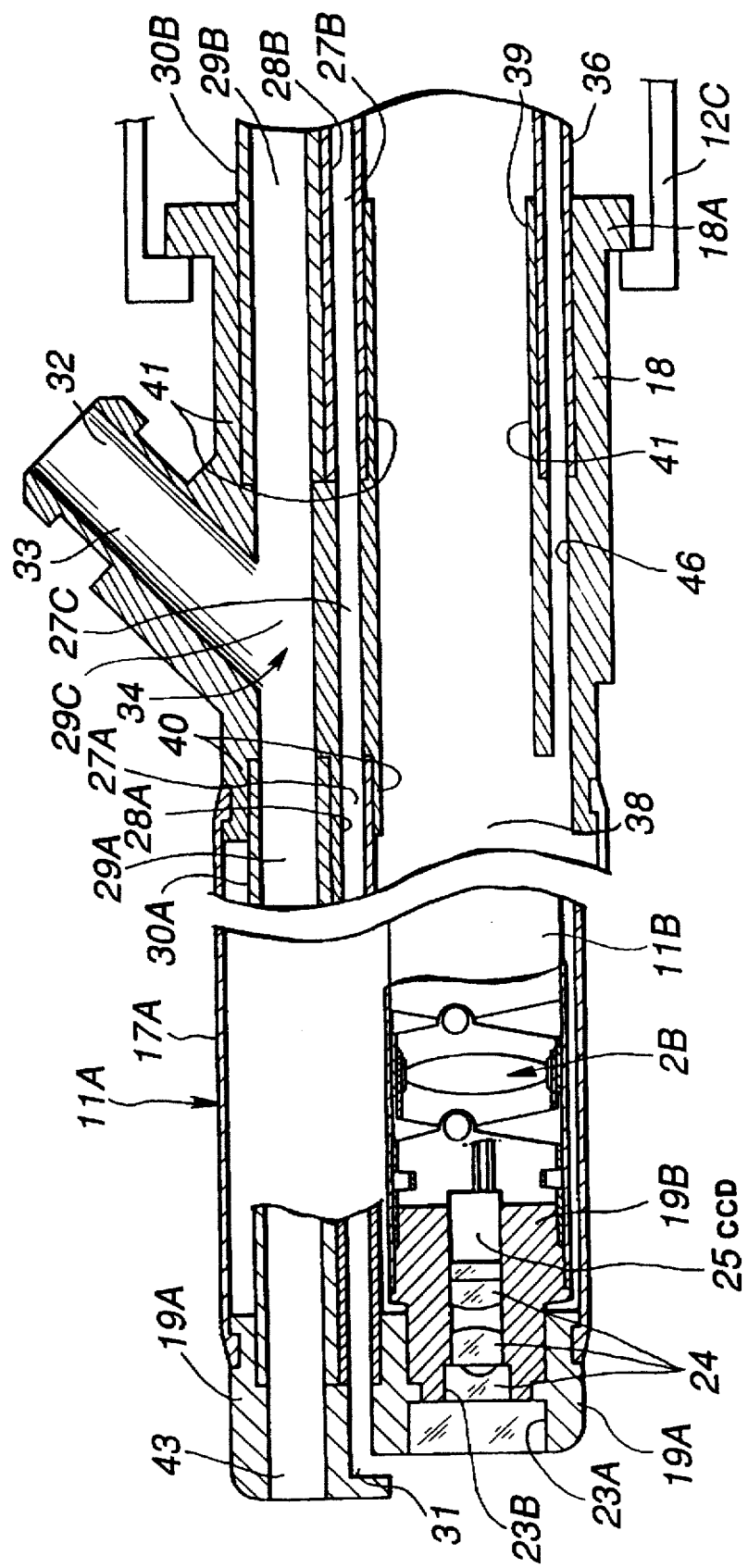
FIGS. 5 and 6 relate to a second embodiment of the endoscope cover apparatus according to the present invention, where
Figure 6:
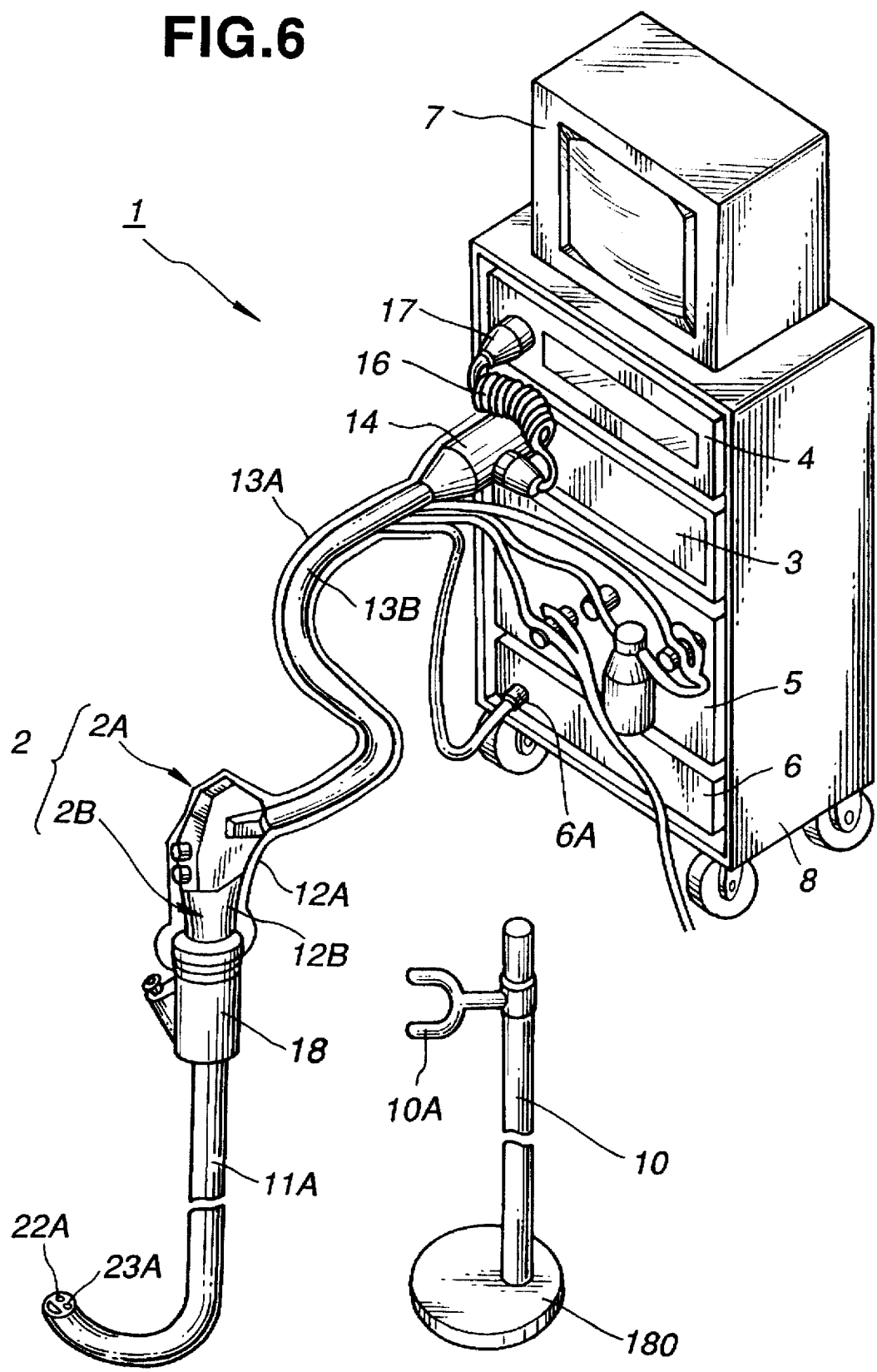

FIGS. 5 and 6 illustrate an endoscope cover apparatus according to a second embodiment of the present invention. FIG. 5 is a cross section view which illustrates the endoscope cover apparatus. FIG. 6 is an overall view which illustrates the shape of a cover-type endoscope apparatus which comprises the endoscope cover apparatus shown in FIG. 5. The overall structure of the endoscope cover apparatus shown in FIG. 5 is structured substantially similarly to that according to the first embodiment. Therefore, the same elements are given the same reference numerals and descriptions will be made about only the different elements.

As shown in FIG. 5, the endoscope cover apparatus according to this embodiment comprises the insertion-portion cover 11A including the air/water supply tube 28A serving as the first tubular passage members, and the suction tube 30A serving as both a forceps insertion tube and a suction tube which, respectively, have the first air/water supply tubular passage 27A and the first suction tubular passage 29A. The leading portion of the first air/water supply tubular passage 27A is connected to the nozzle 31 of the cover leading portion 19A. Furthermore, the leading opening of the nozzle 31 faces the outer surface of the cover observation window 23A.

The base portions of the first air/water supply passage tube 28A and the first suction tube 30A are connected to the fixing joint portion 18 by the joint leading-portion connection portion 40 formed in the leading portion of the fixing joint portion 18.

The first air/water supply tube 28A and the first suction tube 30A are connected to the third air/water supply tubular passage 27C and the third suction tubular passage 29C formed in the fixing joint portion 18. Therefore, the first air/water supply tubular passage 27A is connected to the third air/water supply tubular passage 27C of the fixing joint portion 18 via the second air/water supply tubular passage 27B to be described later. The second air/water supply tube 28B having the second air/water supply tubular passage 27B is extended from the end portion of the fixing joint portion 18 toward the external device in such a manner that it is extended toward the fluid control device 5 while being covered with the universal cord cover portion 13A together with the universal cord 13B. As a result, the base portion of the air/water supply tube 28B is connected to the fluid control device 5. Therefore, body fluid which is adhered to the cover observation window 23A can be removed by supplying air or water via the air/water supply tubular passages 27B, 27C and 27A.

The fixing joint portion 18 has the air/water supply passage 27C and the suction tubular passage 29C as third tubular passages. The fixing joint portion 18 has the endoscope insertion channel 38 for inserting the cover-type endoscope and the expansion tubular passage 46 connected to the endoscope insertion channel 38. The fixing joint portion 18 has the forceps insertion port 32 in the outer top surface thereof. The forceps insertion port 32 joins the third suction tubular passage 29C via the forceps insertion branching portion 34, followed by opening into a forceps port outlet port 43 also serving as a suction port in the cover leading portion 19A. As a result, a forceps and a curing tool inserted through the forceps insertion port 32 pass through a forceps tubular passage 33, the third suction tubular passage 29C and the first suction tubular passage 29A (a forceps channel), followed by projecting over the forceps port 43.

In a portion more closely adjacent to an operator than the fixing joint portion 18, the second air/water supply tube 28B and the second suction tube 30B are disposed, the second air/water supply tube 28B and the second suction tube 30B being respectively connected to the air/water supply tubular passage 27C and the suction tubular passage 29C serving as the third tubular passages of the fixing joint portion 18. The second air/water supply tube 28B and the second suction tube 30B are connected to the fixing joint portion 18 by a joint bonding portion 41 adjacent to an operator. Therefore, the air/water supply tubular passage 27C and the suction tubular passage 29C serving as the third tubular passages, respectively, are connected to the second air/water supply 28B and the second suction tube 30B.

The fixing joint portion 18 has, in a portion adjacent to the operator, the expansion tube 36 serving as a connection tubular passage to be connected to the expansion tubular passage 46. The leading portion of the expansion tube 36 is connected to the fixing joint portion 18 by the joint bonding portion 41 adjacent to an operator. Therefore, the expansion tube 36 serving as the connection tubular passage is connected to the expansion tubular passage 46 and the endoscope insertion channel 38. Furthermore, the expansion tube 36 is extended from the end portion of the fixing joint portion 18 toward the external device similarly to the second suction tube 30B and the second air/water supply tube 28B in such a manner that it is extended while being covered with the universal cord cover portion 13A together with the universal cord 13B. As a result, the base portion of the expansion tube 36 is connected to an expansion tube joint 6A provided for the expander 6 serving as the external device. Therefore, when the cover-type endoscope 2B is inserted (fastened) or removed from the insertion-portion cover 11A, air supplied from the expander 6 is supplied into the endoscope insertion channel 38 via the expansion tube 36 in the universal cord cover portion 13A and via the expansion tubular passage 46. Hence, the insertion-portion cover outer case 17A of the insertion-portion cover 11A is expanded so that the cover-type endoscope 2B can be easily inserted/removed.

The fixing joint portion 18 has, at an end portion thereof, an opening 39 of the endoscope insertion channel 38 for inserting/removing (attaching/detaching) the insertion portion 11B of the cover-type endoscope 2B. The endoscope insertion channel 38 corresponds to a space resulted by omitting the air/water supply tubular passages (27A to 27C) and the suction tubular passages (29A to 29C) from an internal space surrounded by the leading portion 19A, the insertion-cover portion cover outer case 17A and the fixing joint portion 18. The endoscope insertion channel 38 is a portion into which the cover-type endoscope 2B is inserted. Furthermore, the fixing joint portion 18 has a flange portion on the outer periphery thereof. The flange portion 18A is hooked and held by a semicircular holding portion provided for an endoscope cover holding apparatus 10 when, for example, the cover-type endoscope 2B is inserted (fastened) or removed from the endoscope cover 2A.

Then, an example when the thus structured endoscope cover 2A shown in FIG. 5 is used at the time of an endoscope inspection will now be described with reference to FIG. 6.

When the cover-type endoscope 2B is inserted (fastened) into the insertion-portion cover 11A of the endoscope cover 2A, the flange portion 18A of the fixing joint portion 18 is held by the semicircular holding portion 10A provided for the endoscope cover holding device 10. As a result, the insertion-portion cover 11A is fixed.

When an end portion of the expansion tube 36 extending from an end portion of the fixing joint portion 18 to pass through the control-portion cover 12A and the universal cord cover portion 13A is connected to the expansion tube joint 6A (see FIG. 6) provided for the cover expander 6 serving as the external device, air is supplied to the endoscope insertion channel 38 from the cover expander 6. Air thus supplied leaks outside through the opening portion 39.

When the cover-type endoscope 2B is inserted into the opening portion 39, the portion including the opening portion 39 is substantially closed. As a result, air passes the endoscope insertion channel 38, causing the insertion-portion cover outer case 17A to be expanded. Hence, the endoscope insertion portion 11B can be smoothly inserted.

After the insertion operation has been completed, the end portion of the expansion tube 36 is removed from the expansion tube joint 6A, resulting in leakage of air from the expansion tube 36 through the expansion tubular passage 46. As a result, the insertion-portion cover outer case 17A is contracted due to the elasticity thereof (the outer diameter of the insertion-portion cover outer case 17A is reduced). Therefore, the outer surface of the endoscope insertion portion 11B, that is, the outer periphery of the insertion portion 11B is substantially in hermetic contact with the inner surface of the insertion-portion cover outer case 17A.

Although omitted from illustration, the control-portion cover 12A and the insertion-portion cover 11A are then connected to each other by fastening to each other, the control-portion cover fastening portion 12C provided in the leading portion of the control-portion cover 12A and the flange portion 18A provided for the fixing joint portion 18. Thus, the control-portion cover 12A and the insertion-portion cover 11A are connected to each other, followed by covering the cover-type endoscope 2B with the endoscope cover 2A.

Although omitted from illustration, the suction tube 30B and the air/water supply tube 28B extending from the base portion of the fixing joint portion 18 pass through the control-portion cover 12A, followed by extending toward the external device together with the universal cord 13B in such a manner that they are covered with the universal cord cover 13A. As a result, the base portions of the suction tube 30B and the air/water supply tube 28B are connected to the fluid control device 5 serving as the external device.

When the cover-type endoscope 2B is removed from the insertion-portion cover 11A after the inspection with the endoscope has been completed, a holding device (omitted from illustration) having the same shape as that of the foregoing cover holding device 10 is used, resulting in removal of the cover-type endoscope 2B in the foregoing procedure.

This embodiment has the foregoing arrangement that the fixing joint portion 18 includes the expansion tubular passage 46 connected to the endoscope insertion channel 38, the expansion tube 36 serving as the connection tubular passage connected to the expansion tubular passage 46 is extended toward the external device while being covered with the control-portion cover portion 12A and the universal cord cover portion 13A, and the base portion is connected to an expansion tube joint 6A (a clean region) of the cover expander 6 serving as the external device. Therefore, the expansion tube 36 cannot be contaminated from outside and can be easily kept clean. Since the expansion tube 36 is connected to the expansion tube joint 6A which is the clean region, the expansion tube 36 and the expansion tube joint 6A do not become contaminated regions.

That is, when the cover-type endoscope 2B is inserted (fastened) into the insertion-portion cover 11A, the expansion tube 36, which is the clean region, and the expansion tube joint 6A, which is the clean region, are connected to each other. After the insertion has been made, the expansion tube 36 is removed from the expansion tube joint 6A, causing the expansion tube 36 to be a clean region at this time.

Since the expansion tube 36 is covered with the endoscope cover 2A, as shown in FIG. 5 during the inspection, the clean state can be maintained, that is, contamination of the expansion tube 36 from outside can be prevented. Because cover-type endoscope 2B is removed after the inspection has been completed, resulting in an establishment of the connection between the expansion tube 36, which is the clean region, and the expansion tube joint 37, which is the clean region. Also in this case, both of the expansion tube 36 and the expansion tube joint 6A are clean and freed from the contamination.

The used endoscope 2A is disposed, for example, at the time of performing another inspection, and a new endoscope cover 2A is used. Because the endoscope cover 2A, that is, the expansion tube 36, is newly provided at each inspection, a clean state is, of course, realized. As a result, the contamination of the expansion tube 36, the expansion tubular passage 46 and the endoscope insertion channel 38 can be prevented at the time of the inspection. Further, the contamination of the cover-type endoscope 2B to be inserted into the endoscope insertion channel 38 can also be prevented.

Since this embodiment has an arrangement in which the expansion tube 36 is integrally provided in the endoscope cover 2A, it can be made disposable similarly to the endoscope cover 2A. Furthermore, the contaminated regions except for the insertion-portion cover 11A of the endoscope cover 2A are held by the holding member 10A provided for the holding device 10, resulting in prevention of external contamination. Moreover, the necessity of cleaning and disinfecting the expander connection tube at each inspection, which has been required in the related art, can be eliminated. When the cover-type endoscope 2B is inserted (fastened) into the insertion-portion cover 11A of the endoscope cover 2A, only the end portion of the expansion tube 36 must be simply connected/disconnected from the cover expander. Therefore, the operation can be easily completed.

Figure 7:
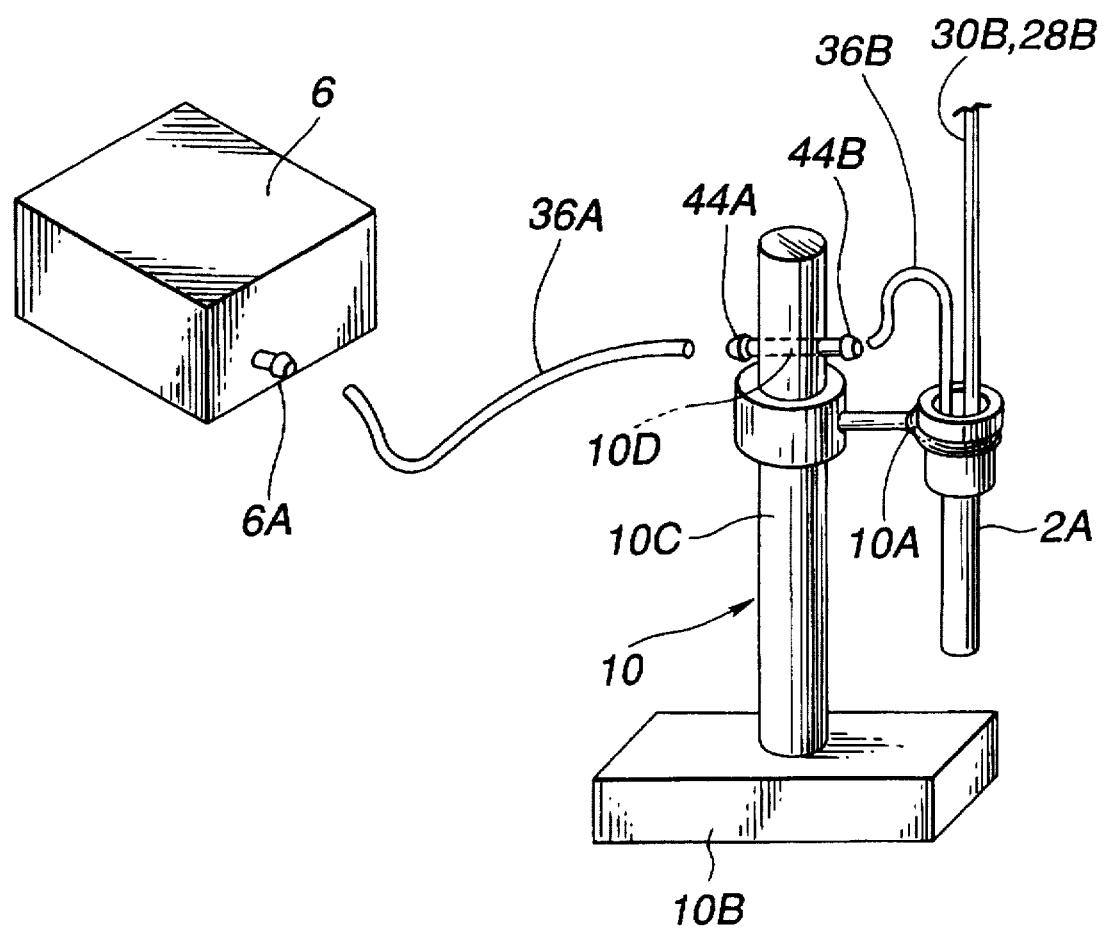
FIG. 7 relates to a third embodiment of the endoscope cover apparatus according to the present invention wherein a case is illustrated in which an endoscope cover holding device is used.

FIG. 7 illustrates a third embodiment of the endoscope cover apparatus according to the present invention. FIG. 7 is a perspective view which illustrates an example of the endoscope cover holding device 10 provided for the purpose of cleanly attaching/detaching the cover-type endoscope 2B to and from the endoscope cover 2A.

Referring to FIG. 7, the endoscope cover holding device 10 has a mounting member 10B which has an elongated support rod 10C, bonded to it, standing erect in the vicinity of the central portion of the top surface of the mounting member 10B. Furthermore, the endoscope cover holding device 10 has a holding portion 10A which is adjustable in height by, for example, vertically sliding the support rod 10C. The leading portion of the holding portion 10A is formed into, for example, a semicircular shape, while the base portion extending from the leading portion is formed into an annular shape. Thus, the base portion is fitted around the support member 10 and is capable of sliding along it. The holding member 10A has a fastening member (omitted from illustration) for holding a predetermined height.

In the upper portion of the support rod 10C, a penetrating tubular passage 10D is formed to laterally penetrate the support rod 10C. Furthermore, each through-hole has a connection tube joint 44A and a connection tube joint 44B at the two ends thereof.

This embodiment has an arrangement in which the expansion tube 36 extending from the endoscope cover 2A and serving as the connection tubular passage is divided into an expansion tube 36A adjacent to the expander and an expansion tube 36B adjacent to the endoscope cover. The leading portion of the expansion tube 36A is connected to the connection tube joint 44A, while the base portion is connected to the expansion tube joint 6A provided for the expander 6. As a result, the connection tube joint 44A, the expansion tube 36A and the expansion tube joint 6A of the cover expander 6 are connected to one another. Furthermore, the base portion of the expansion tube 36B integrally formed with the endoscope cover 2A is connected to the connection tube joint 44B, as shown in FIG. 7.

The endoscope cover holding device 10 thus structured is used at the time of inserting (fastening) the cover-type endoscope 2B into the insertion-portion cover 11A.

After the inspection with the endoscope has been completed, the flange portion 18A (see FIG. 5) provided in the base portion of the used insertion cover portion 11A is held while being hooked by the holding portion 10A provided for the endoscope cover holding device 10 as shown in FIG. 7.

Then, the base portion of the expansion tube 36B extending from the end portion of the insertion-portion cover 11A is connected to the connection tube joint 44B provided for the endoscope cover holding device 10. Then, the expansion tube 36A is connected to the expansion tube joint 6A provided for the cover expander 6, while the end portion is connected to the connection tube joint 44A provided for the endoscope cover holding device 10. As a result, air from the cover expander 6 is supplied to the expansion tube 36B through the expansion tube joint 6A via the expansion tube 36A, the connection tube joint 44A and the connection tube joint 44B. That is, air is supplied to the endoscope insertion channel 38 (see FIG. 5) connected to the expansion tube 36B to expand the cover-portion outer case 17A (see FIG. 5) of the insertion-portion cover 11A. As a result, the cover-type endoscope 2B can easily be removed.

Accordingly, this embodiment enables the expansion tube 36B extending from the end portion of the insertion-portion cover 11A to be kept clean because it is covered with the universal cord cover 13A similarly to the second embodiment. Furthermore, the connection tube joint 44B of the endoscope cover holding device 10 connected to it is also clean and is not contaminated. In addition, the cover expander 6 and the expansion tube joint 6A provided for the cover expander 6 are clean. Moreover, the expansion tube 36A and the connection tube joint 44A connected to the expansion tube joint 6A are clean and are not contaminated.

As a result, the contaminated region except for the insertion-portion cover 11A of the endoscope cover 2A is restricted to the holding member 10A provided for the holding device 10. Therefore, the external contamination can be prevented, and the insertion (fastening) and removal of the cover-type endoscope 2B to and from the insertion-portion cover 11A can be performed cleanly while being freed from the contamination.

The embodiment may be arranged to shorten the expansion tube 36 to be easily covered with the universal cord cover 13A.

Although the above description describes the second embodiment comprising the third tubular passage member of the fixing joint portion 18, a joint port or the like may be formed which is opened in the outer surface of the fixing joint portion 18, connected to the third tubular passage member and which has another function.

Although the third embodiment has an arrangement in which the expansion tube 36 extending from the end portion of the endoscope cover 2A and serving as the connection tubular passage is separated, another connection member may be used for the expansion tube 36A connected to the expander 6 and the connection tube joint 44A if the expander 6 and the connection tube joint 44A of the endoscope cover holding device 10 are connected to each other followed by connecting to the expansion tube 36 of the endoscope cover 2A.

Figure 8:
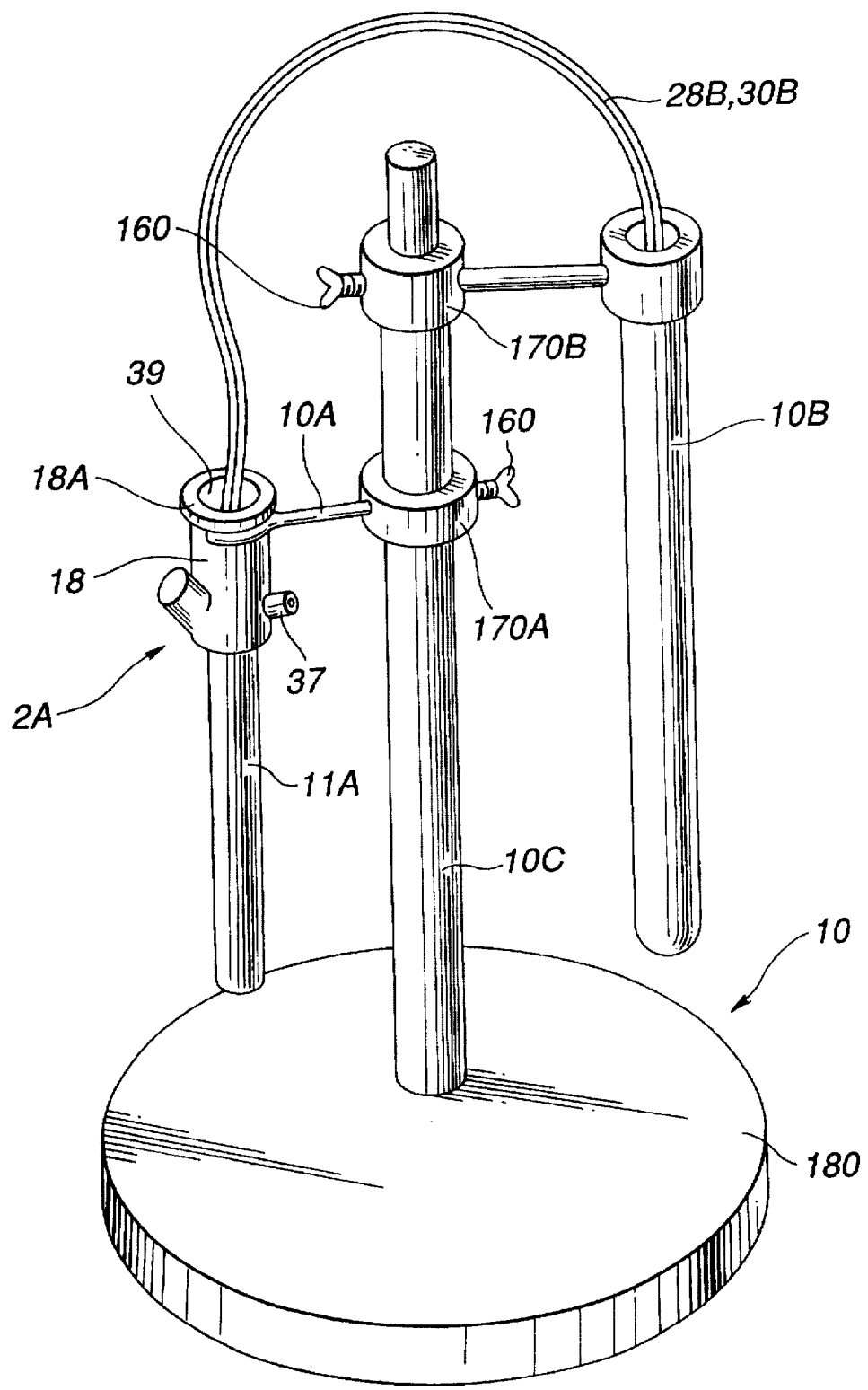
FIGS. 8 and 9 relate to a fourth embodiment of the endoscope cover holding device according to the present invention, where

Then, the cover holding device 10 for use at the time of inserting (fastening) the cover-type endoscope 2B into the endoscope cover 2A is shown in FIG. 8.

Figure 9:
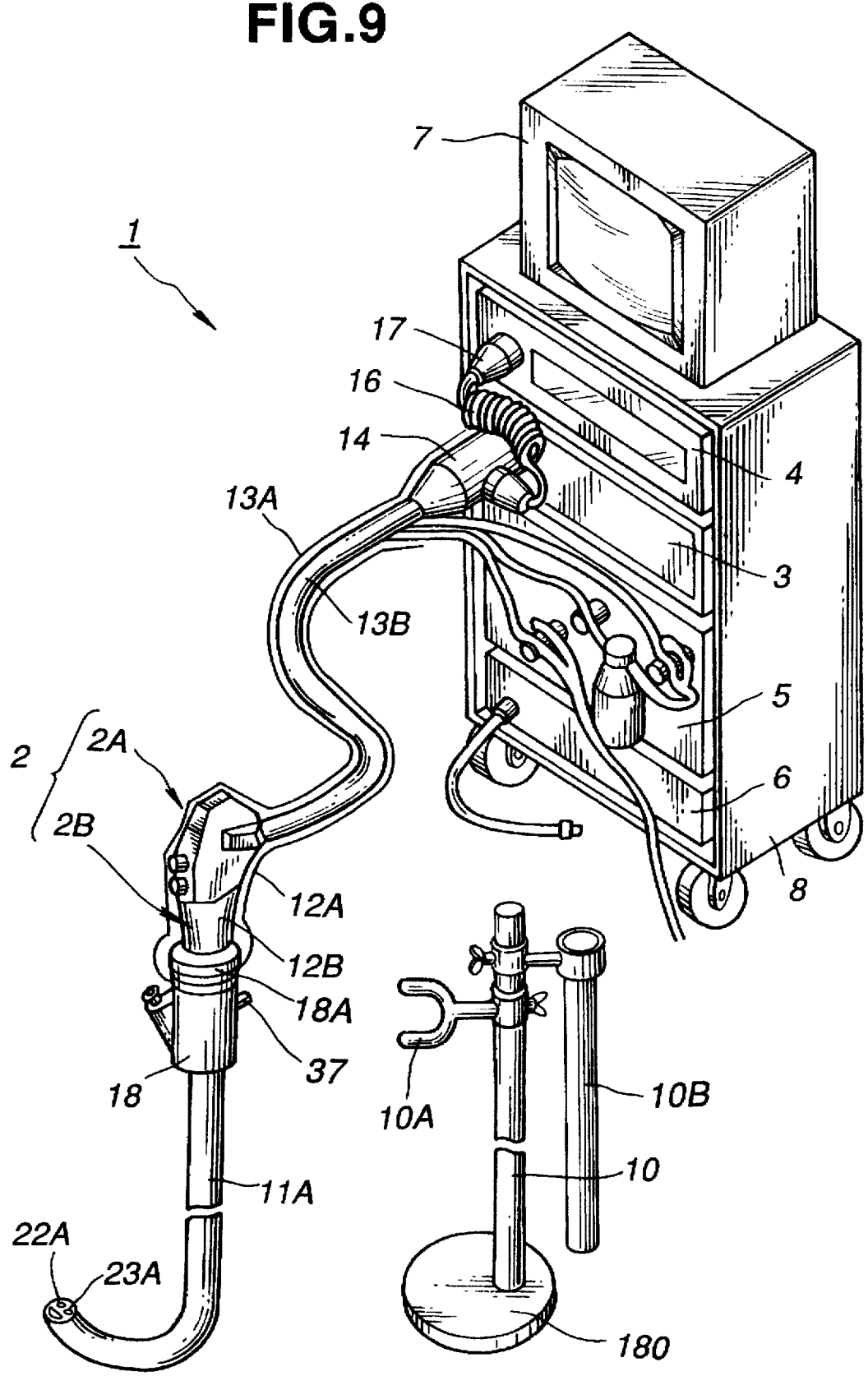

FIGS. 8 and 9 illustrate an endoscope cover holding device according to a fourth embodiment of the present invention. FIG. 8 is a perspective view which illustrates an endoscope cover holding device. FIG. 9 is a view which illustrates the overall shape of a cover-type endoscope apparatus which uses the endoscope cover holding device shown in FIG. 8.

Referring to FIG. 8, the cover holding device 10 according to this embodiment has, for example, a mounting 180. The mounting 180 has a support rod 10C fastened vertically. The support rod 10C has an adjuster 170A capable of vertically sliding along the support rod 10C. The adjuster 170A enables a height adjustment to be performed, and the realized height is maintained by a fixing screw 160 driven as shown in FIG. 8. The adjuster 170A has a holding portion 10A (see FIG. 9) formed into a semicircular shape in the leading portion of a supporting member extending horizontally from the outer surface of the adjuster 170A. The holding portion 10A is used to fasten a flange portion 18A formed, for example, in the end portion of the endoscope cover 2A. That is, the flange portion 18A of the endoscope cover 2A is hooked by the holding portion 10A so that the endoscope cover 2A can be held while preventing separation. When the cover-type endoscope 2B is, from an upper portion, inserted through the opening 39 of the endoscope cover 2A in the foregoing state, the cover-type endoscope 2B and the endoscope cover 2A can be fastened while preventing contamination.

Another adjuster 170B is disposed above the adjuster 170A, the adjuster 170B also being capable of vertically sliding along the support rod 10C. As a result, the height can be adjusted and the realized height can be maintained in such a manner that it is secured by a fixing screw 160. Furthermore, the leading portion of a support member extending horizontally from the outer surface of the adjuster 170B has an annular accommodating member 10B having an opening in the top end thereof and a closed bottom portion fastened thereto as shown in FIG. 8. The accommodating member 10B is arranged so that it accommodates the base portions of the air/water supply tube 28B and the suction tube 30B extending from the end portion of the endoscope cover 2A held in the space by the annular holder 10B having the closed bottom end. The shape of the accommodating member 10B may be formed arbitrarily while accommodating the air/water supply tube 28B and the suction tube 30B.

Then, an example will be described in which the cover-type endoscope is fastened to the endoscope cover by using the endoscope cover holding device shown in FIG. 8.

First, the adjustment member 170A slidably fastened to the support rod 10C is shifted to a height at which the insertion-portion cover 11A of the endoscope cover 2A is held at the space, followed by fixing the adjustment member 170A with the fixing screw 160.

Then, the insertion-portion cover 11A of a clean endoscope cover 2A is taken out from a cover package (omitted from illustration), followed by a fastening action in which the flange portion formed in the end portion of the endoscope cover 2A is hooked to the semicircular holding portion 10A of the endoscope cover holding device. Simultaneously, the base portions of the tubular passages, such as the air/water supply tube 28B and the suction tube 30B extending from the end portion of the endoscope cover 2A, are accommodated in the accommodating member 10B. As a result, the endoscope cover 2A is brought into a state where it is held by the holding portion 10A in the space. By accommodating the tubular passages extending from the endoscope cover 2A in the accommodating member 10B, the foregoing tubular passages can be supported in a clean, uncontaminated state.

In the foregoing state, an expander connection tube (omitted from illustration) is connected to the expansion tube joint 37 provided for the endoscope cover 2A, followed by connecting another end portion to the cover expander 6. As a result, air is supplied from the cover expander 6, and, in this state, the cover-type endoscope 2B (omitted from illustration) is inserted from the opening 39 of the endoscope cover 2A. As a result, the insertion-portion cover 11A of the endoscope cover 2A is brought into an expanded state so that the cover-type endoscope can easily be fastened. Then, the removal of the expander connection tube (omitted from illustration) from the expansion tube joint 37 causes the outer case of the insertion-portion cover to be contracted. As a result, the cover-type endoscope is covered. Therefore, the cover-type endoscope 2B and the endoscope cover 2A cannot be contaminated, and accordingly, fastening of the endoscope cover 2A to the cover-type endoscope 2B can be performed in a clean state.

Figure 13:
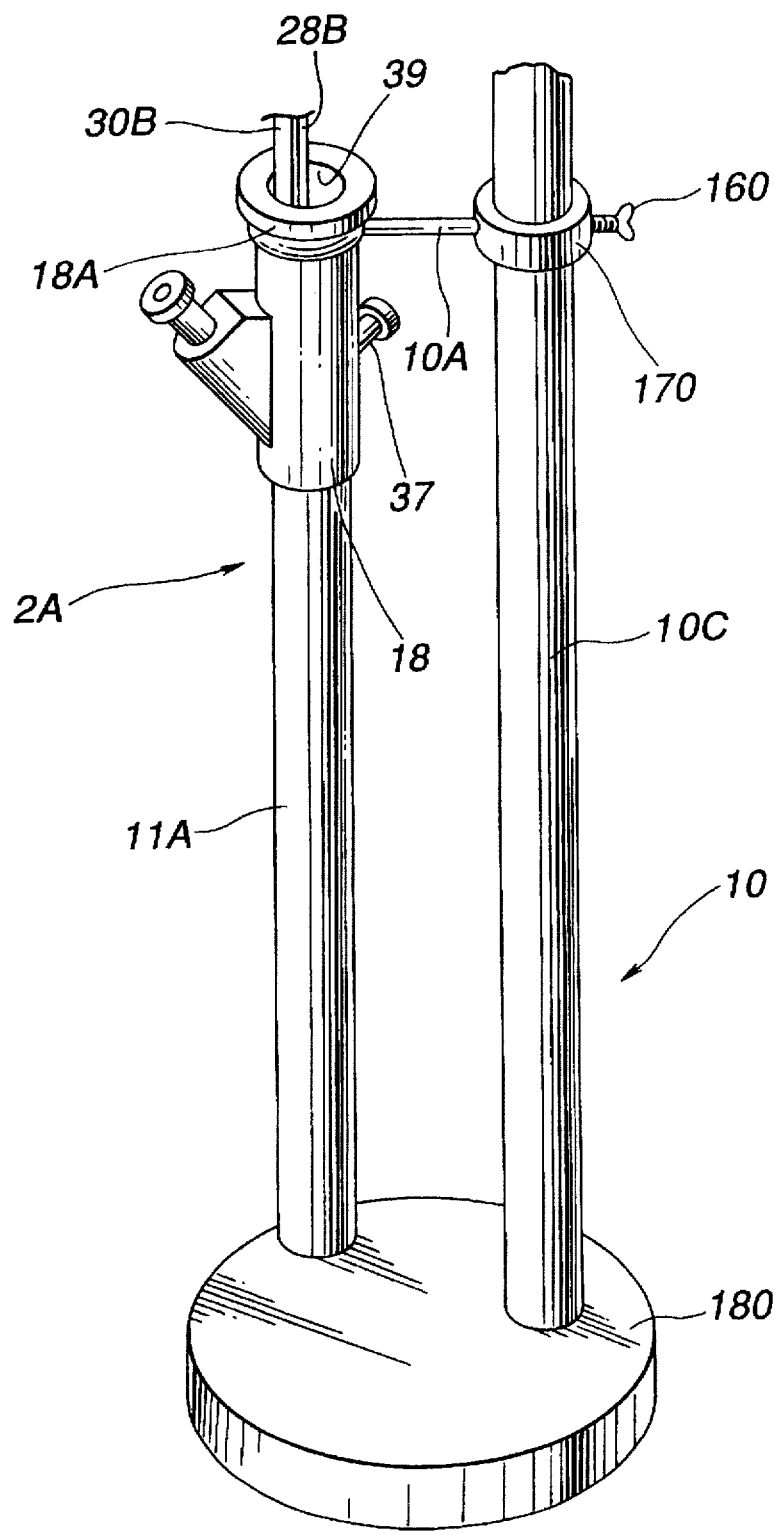
FIG. 13 is a perspective view which illustrates an endoscope cover holding device according to a related art.
Figure 14:
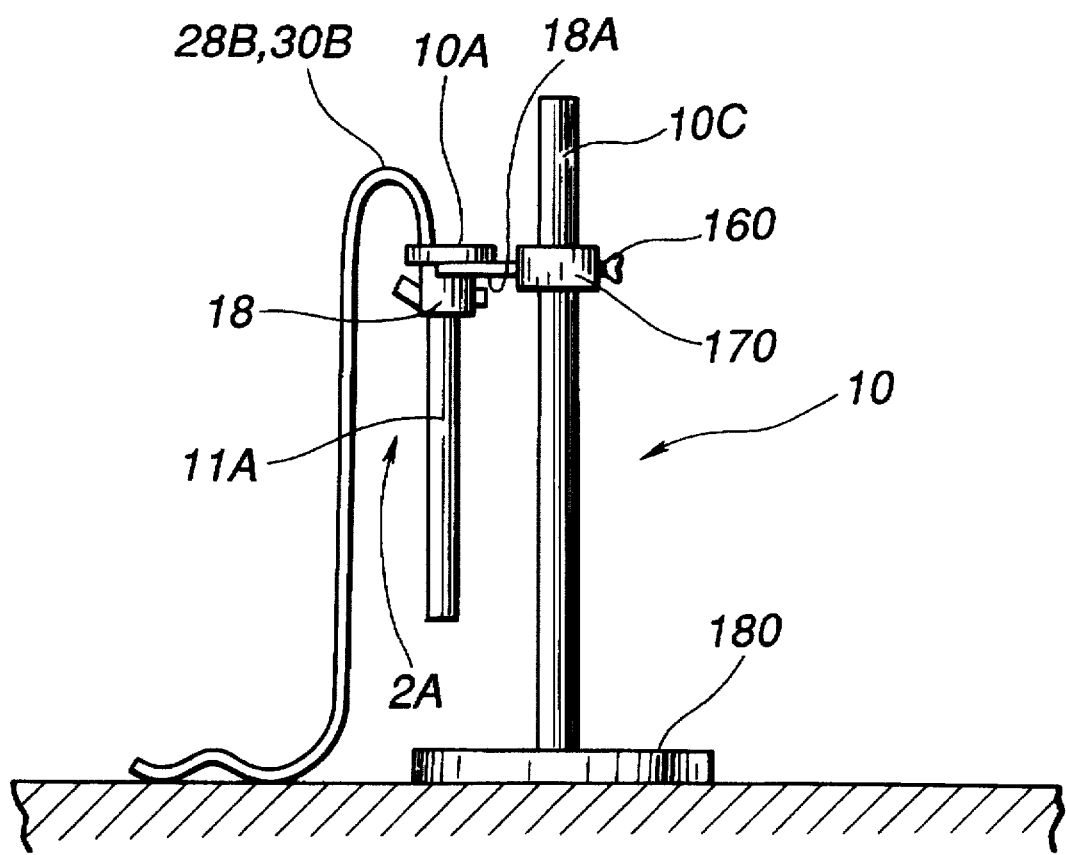
FIG. 14 illustrates the method of use of the endoscope cover holding device according to the related art.

Although the cover holding device 10, which is an example of the related art and is shown in FIG. 13, and which has no accommodating member 10A, is able to hold the endoscope cover 2A in the space by the holding portion 10A at the time of inserting the cover-type endoscope 2B into the insertion-portion cover 11A of the endoscope cover 2A, no member is provided to support the base portions of the tubular passages such as the air/water supply tube 28B and the suction tube 30B extending from the end portion of the endoscope cover 2A. Moreover, the foregoing tubular passages are elongated members, which can be connected to the external device, resulting in sufficient attention to be paid to prevent contact with unclean regions, such as the floor and the wall as shown in FIG. 14 in order to perform a safety inspection.

Therefore, this embodiment has an arrangement in which the adjustment member 170B and the accommodating member 10B are provided in addition to the adjustment member 170A and the holding portion 10A is able to accommodate and support the base portions of the tubular passages extending from the outer portion of the endoscope cover 2A held by the holding portion 10A in the space. Therefore, the base portions of the tubular passages are not in contact with the unclean regions such as the floor and the wall. Hence, the work for fastening the cover to the cover-type endoscope can be performed cleanly and safely. That is, the contamination occurring from the tubular passages can be prevented, and the work for fastening the cover to the cover-type endoscope 2B can easily be performed.

This embodiment may have an arrangement in which the accommodating member 10B is made detachable from the supporting member of the adjuster 170B for the purpose of easily performing the cleaning and disinfecting.

Figure 10:
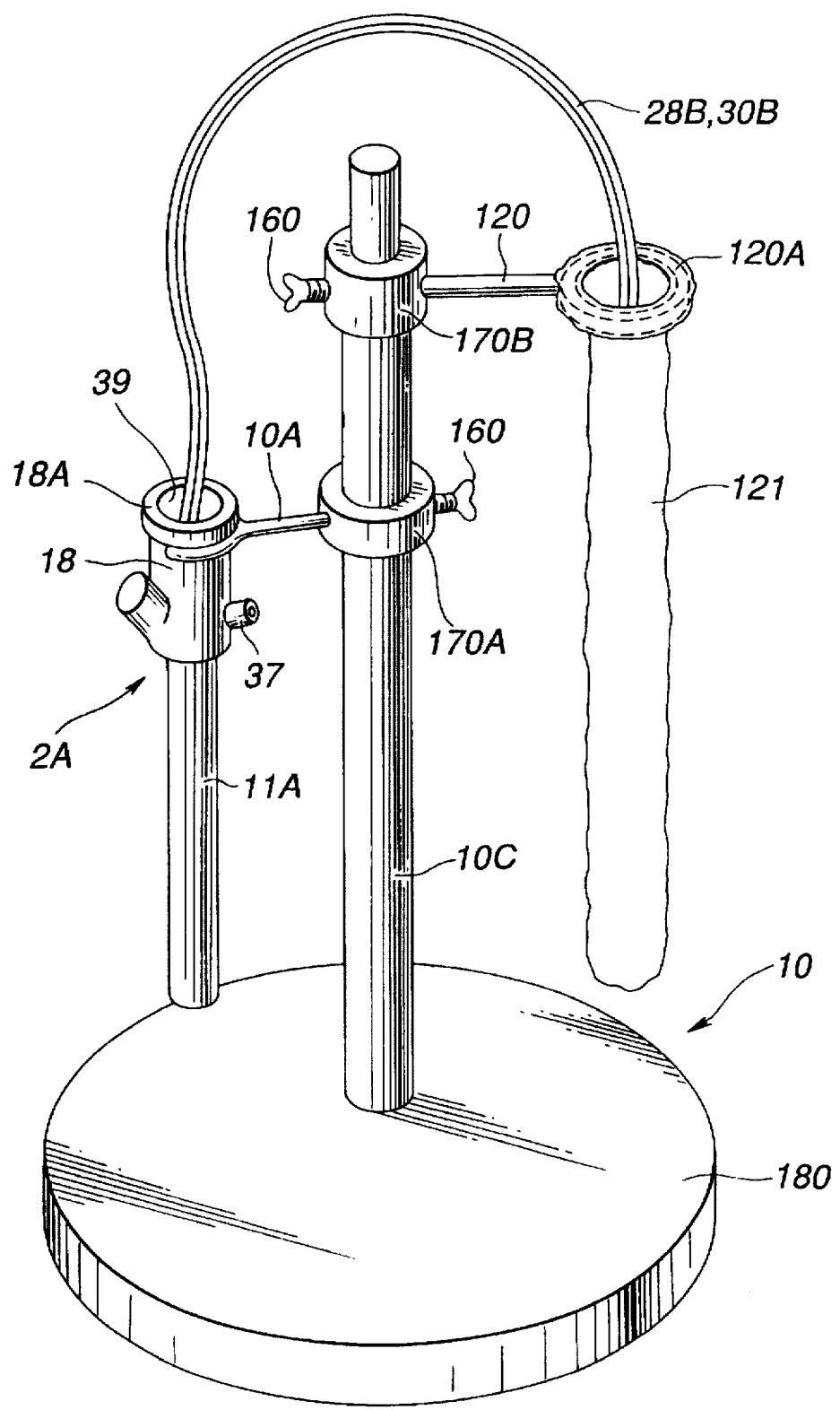
FIG. 10 relates to a fifth embodiment of the endoscope cover holding device according to the present invention and is a perspective view which illustrates the structure of the endoscope cover holding device.

FIG. 10 illustrates a fifth embodiment of the endoscope cover holding device according to the present invention. FIG. 10 is a perspective view which illustrates an improvement in the accommodating member of the endoscope cover holding device shown in FIG. 8.

The endoscope cover holding device 10 comprises an annular holding portion 120 and a disposable accommodating bag 121 fastened around it employed in place of the holding portion 10A of the endoscope cover holding device 10 shown in FIG. 8.

The annular holding portion 120 has the adjuster 170B slidable along the support rod 10C similarly to the fourth embodiment. As a result, the height can be adjusted, followed by fixing by using the fixing screw 160. Furthermore, the annular holding portion 120 horizontally extending from the outer surface of the adjuster 170B forms an annular portion 120A formed into the annular shape.

The annular portion 120A of the annular holding portion 120 has an accommodating bag 121 formed into a disposable bag shape. The accommodating bag 121 is fastened by winding the opened end of the accommodating bag 121 around the annular portion 120A of the annular holding portion 120. The accommodating bag 121 is made of synthetic resin, or natural resin or paper. The other structures and operations are the same as those of the fourth embodiment, and therefore their descriptions are omitted here.

Therefore, according to this embodiment, the adjuster 170B, the annular holding portion 120 and the accommodating bag 121 fastened to it are provided in addition to the adjuster 170A and the holding portion 10A similarly to the fourth embodiment so that the base portions of the tubular passages extending from the outside of the endoscope cover 2A held in the space by the holding portion 10A can be accommodated and supported. The accommodating member 10B according to the fourth embodiment suffers from a tendency to accumulate dust. However, the accommodating bag 121 according to this embodiment can be made disposable, resulting in a clean state of use because no dust is accumulated. Therefore, the base portions of the tubular passage are not in contact with the unclean regions such as the floor and the wall, and accordingly, the work for fastening the endoscope cover 2A to the cover-type endoscope 2B can be performed cleanly and safely. That is, the contamination from the tubular passages can be prevented and the work for fastening the endoscope cover 2A to the cover-type endoscope 2B can easily be performed.

Figure 11:
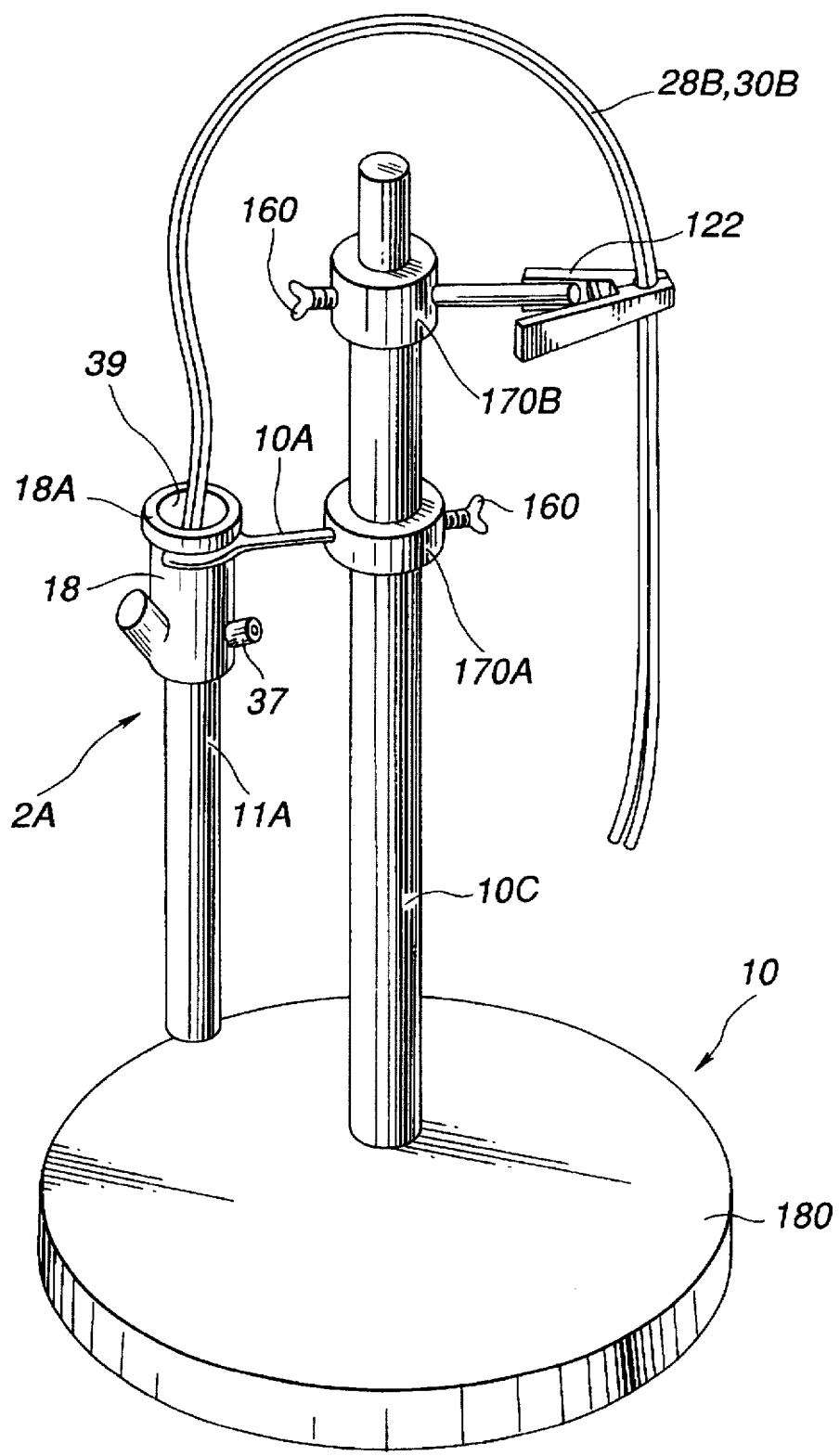
FIG. 11 relates to a sixth embodiment of the endoscope cover holding device according to the present invention and is a perspective view which illustrates the structure of the endoscope cover holding device.

FIG. 11 illustrates a sixth embodiment of an endoscope cover holding device according to the present invention. FIG. 11 is a perspective view which illustrates an example of an improvement in the accommodating member of the endoscope cover holding device shown in FIG. 8.

As shown in FIG. 11, the endoscope cover holding device 10 is characterized in that the holding portion 10A of the endoscope cover holding device 10 shown in FIG. 8 is replaced by a holder 122.

In this embodiment, the adjuster 170B which is slidable along the support rod 10C is provided similarly to the fourth embodiment so that height is adjusted and the realized height is held by the fixing screw 160. The support member horizontally extending from the outer surface of the adjuster 170B has, in the leading portion thereof, a holder 122 fastened thereto, the holder 122 having, for example, a pair of holding members, the leading holding portions of which are always urged by a spring in the holding direction. The holder 122 is able to hold tubular passage with minimum force and, accordingly, the operation can be facilitated. The other structure and operations are the same as those of the fourth embodiment, and therefore their descriptions are omitted here.

According to this embodiment, the adjuster 170B and the holder 122 are provided in addition to the adjuster 170A and the holding portion 10A similarly to the fourth embodiment. Therefore, the tubular passages extending from the outside of the endoscope cover 2A held in the space by the holding portion 10A can be held in the space. Therefore, the base portions of the tubular passages are not in contact with the unclean regions such as the floor and the wall. As a result, the work for fastening the endoscope cover 2A to the cover-type endoscope 2B can be performed cleanly and safely. That is, the contamination from the tubular passages can be prevented, and the endoscope cover 2A can easily be fastened to the cover-type endoscope 2B.

Figure 12:
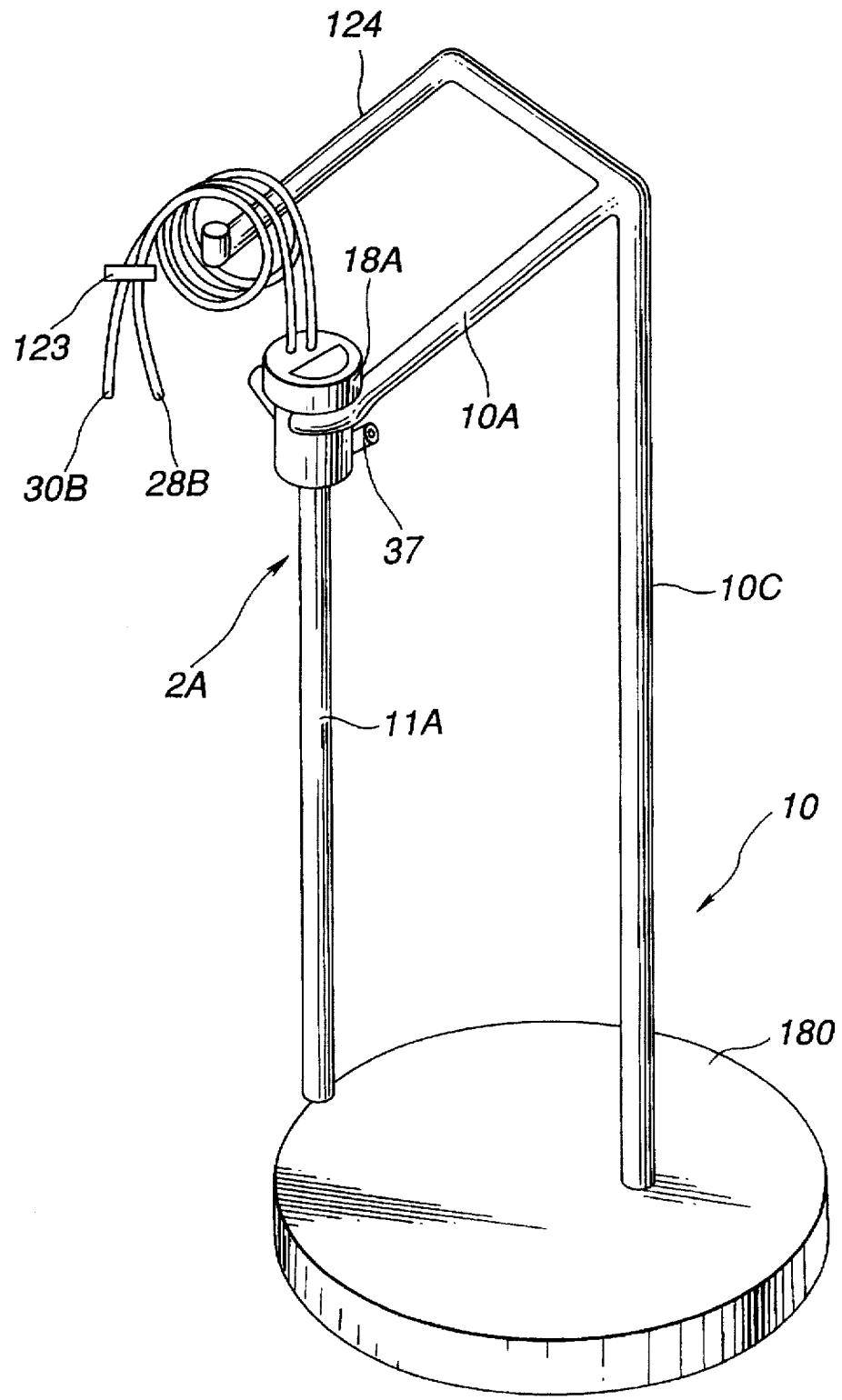
FIG. 12 relates to a seventh embodiment of the endoscope cover holding device according to the present invention and is a perspective view which illustrates the structure of the endoscope cover holding device.

FIG. 12 illustrates a seventh embodiment of the endoscope cover holding device according to the present invention. FIG. 12 is a perspective view which illustrates a case where the supporting rod of the endoscope cover holding device is extended, and a holding portion and a tubular passage fastening arm are provided.

As shown in FIG. 12, the endoscope cover holding device 10 has, for example, a mounting 180. The mounting 180 has a support rod 10C fastened vertically. Supporting members are formed to extend from the top end portion of the support rod 10C while being horizontally branched in two directions apart by an angular degree of 90°, either of which is formed into an inverted C-shape holding portion 10A for holding the endoscope cover 2A and having two end portions bent upward. The residual portion is formed into a shape having a supporting member extending from the support rod 10C into another direction. The supporting member is formed into a tubular passage fastening arm 124 which is bent to run parallel to the holding portion 10A at a position of a predetermined length where the end portion is bent upwards.

The holding portion 10A fastens the flange portion 18A provided for, for example, the end portion of the endoscope cover 2. That is, the flange portion 18A of the endoscope cover 2A is hooked at the holding portion 10A so that the endoscope cover 2A can be held while preventing separation. When the cover-type endoscope 2B is, from an upper portion, inserted through the opening 39 of the endoscope cover 2A in the foregoing state, the cover-type endoscope 2B and the endoscope cover 2A can be fastened to each other while preventing the contamination.

On the other hand, the tubular passage fastening arm 124 is wound several times around the tubular passages such as the air/water supply tube 28B and the suction tube 30B extending from the end portion of the endoscope cover 2A held in the space by the holding portion 10A so that the tubular passages are supported in the space, followed by temporarily binding them by using a binding member 123 such as a tape seal, a band or a string.

Therefore, according to this embodiment, the provided holding portion 10A enables the endoscope cover 2A to be held in the space. The provided tubular passage fastening arm 124 enables the tubular passages extending from the outer surface of the endoscope cover 2A held in the space by the holding portion 10A to be bound and fastened. Furthermore, the use of the binding member 123 enables the tubular passages to be temporarily bound. Therefore, the base portions of the tubular passages do not come in contact with the unclean regions such as the floor and the wall. Hence, the work for fastening the endoscope cover 2A to the cover-type endoscope 2B can be performed cleanly and safely. That is, the contamination from the tubular passage can be prevented, and the work for fastening the endoscope cover 2A to the cover-type endoscope 2A can easily be performed.

This embodiment may have an arrangement in which the supporting rod 10C is divided into an inner cylinder and an outer cylinder having different outer diameters to adjust the height of the supporting rod 10C fastened to the mounting 180, the inner cylinder being received by the outer cylinder. As a result, a slidable type supporting rod is constituted.

The fourth to seventh embodiments have described a structure in which the cover-type endoscope is fastened to the endoscope cover. An effect can, of course, be obtained from the present invention at the time of removing the cover-type endoscope.

Figure 15:
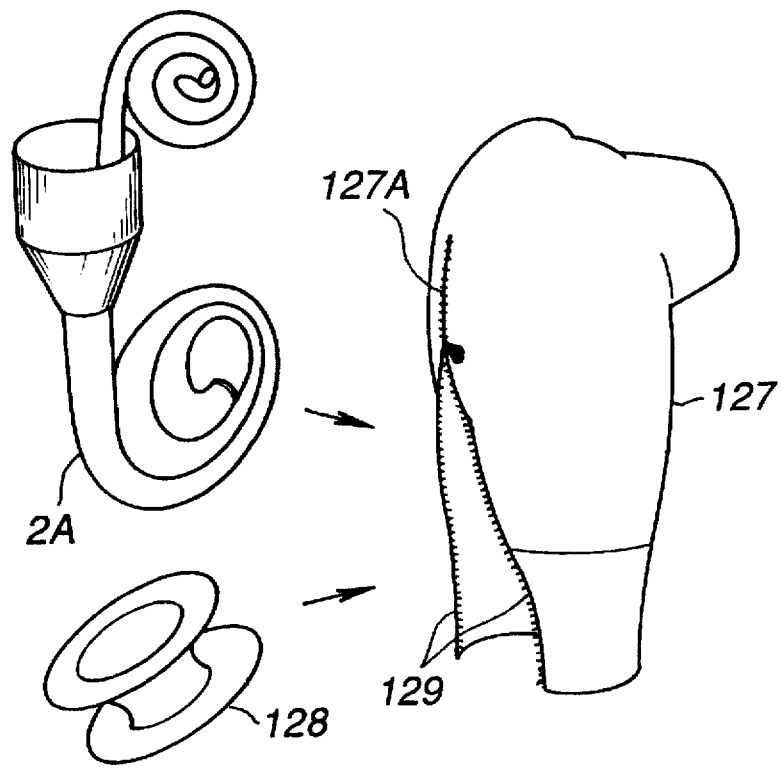
FIG. 15 illustrates a case where other disposable products are accommodated in a control-portion cover.
Figure 16:
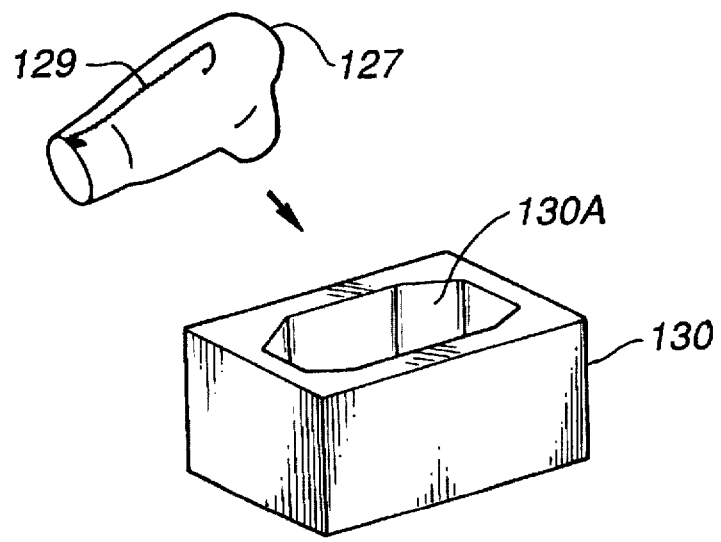
FIG. 16 illustrates a case where the control-portion cover shown in FIG. 15 is packaged.

FIGS. 15 and 16 illustrate an example of simply accommodating the endoscope cover for covering the cover-type endoscope and other disposable products while saving the required space.

FIG. 15 illustrates a case where other disposable products are accommodated in a control-portion cover 127 which is a disposable product. FIG. 16 illustrates a case where the control-portion cover 12 shown in FIG. 15 is packaged.

Referring to FIG. 15, the disposable products are generally classified into the insertion-portion cover 2A of the endoscope cover, the control-portion cover 127 and a disposable mouth piece 128 and the like. The control-portion cover 127 is formed to be a reversible member to cover the control portion of the cover-type endoscope and formed to be an accommodating member. The control-portion cover 127 has a cut portion 127A cut from a position adjacent to the central portion of the outer surface toward the lower end portion, the cut portion 127A being opened considerably. For example, a fastener 129 is provided to cover the two ends of the cut portion 127A. Therefore, the control-portion cover 127 can be closed by the fastener 129. Further, the two sides of the control-portion cover 127 are sterilized.

By using the foregoing control-portion cover 127, the other disposable products, for example, the insertion-portion cover 2A and the disposable piece 128 and the like can be accommodated in the control-portion cover 127 in a compact manner as shown in FIG. 15. Furthermore, the fastener 129 closes the control-portion cover 127 and maintains the accommodated state.

When the control-portion cover 127 accommodating the disposable products is packaged, a package 13 for the control-portion cover is provided as shown in FIG. 16. Further, the control-portion cover 127 accommodating the disposable products is accommodated in the package 130 for the control-portion cover. The package 130 for the control-portion cover has an accommodating chamber 130A, the size and the shape of which are sufficient to accommodate the control-portion cover 127. Therefore, the accommodating work can easily be performed, and the accommodated products can easily be taken out.

The package 130 for the control-portion cover accommodating the control-portion cover 127 is sterilized, followed by covering with, for example, a cover (omitted from illustration) for the package 130 for the control-portion cover or a clean vinyl sheet. That is, the package 130 for the control-portion cover is packaged, followed by delivery to the user while being accommodated in a corrugated board box (omitted from illustration). It should be noted that the foregoing package is maintained in a sterilized state.

At the time of use, the package 130 for the control-portion cover is removed from, for example, the corrugated board box, followed by removing a cover if it is provided. If the vinyl sheet is used to cover the control-portion cover 127, it is removed, followed by taking out the control-portion cover 127. In this case, the control-portion cover 127 does not need to be clean. Then, the fastener 129 of the control-portion cover 127 is opened to take out the accommodated disposable products, that is, the insertion-portion cover 2A and the disposable mouth piece 128 and the like. The foregoing removing operation must be performed in a clean state.

The thus taken out disposable products are fastened to the cover-type endoscope. The control-portion cover 127 is reversed before it is fastened to the endoscope. As the result of reversing, the control-portion cover 127 can be used in a clean state.

Figure 19:
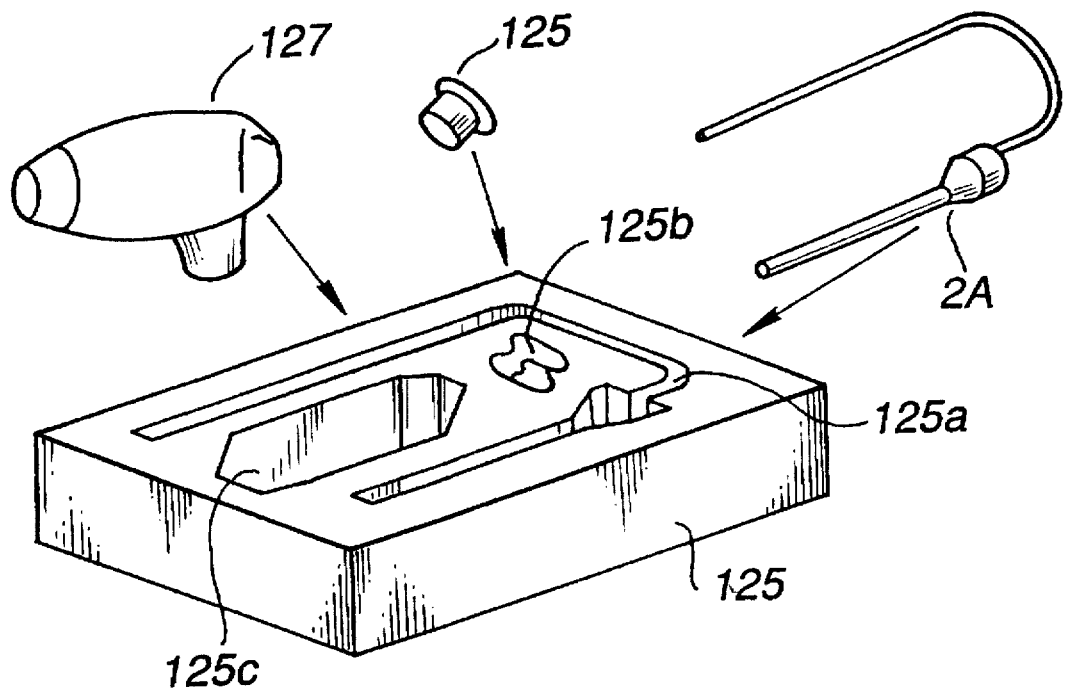
FIG. 19 illustrates a conventional state where the disposable product is packaged.
Figure 20:
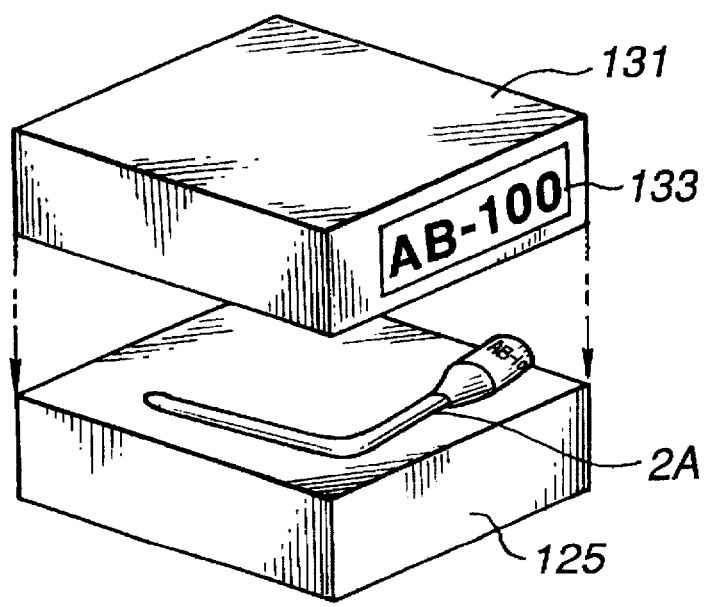
FIG. 20 illustrates a conventional state where the endoscope cover is packaged.

In contrast with the conventional technology in which the disposable products are accommodated in the endoscope cover package 125, as shown in FIG. 19, this embodiment enables the disposable products to be accommodated in one control-portion cover 127 in a compact manner. Furthermore, the size of the package of the disposable products can be reduced. Therefore, a large storage space is required in a facility that has a large number of cases because a large quantity of disposable products are consumed. However, the package of the disposable products according to this embodiment has a small size, and, accordingly, a large storage space does not need to be provided.

Since a conventional endoscope package 125 has accommodating chambers 125A, 125B and 125C for accommodating disposable products as shown in FIG. 19, the manufacturing process becomes complicated and the size cannot be reduced, resulting in a rise in cost. However, this embodiment requires only one accommodating chamber 130A for the package 130 for the control-portion cover. Furthermore, the small size of the package 130 for the control-portion cover enables greater manufacturing facility while reducing cost.

Although the description of this embodiment is about the fastener 129 which is a closing means of the control-portion cover 127, the present invention is not limited to this. For example, a magic tape or an adhesive tape that can easily be removed may be used. If the cut portion 12A can be closed at the time of the accommodation, and if the endoscope control portion can be covered and the covered state can be maintained, another member may be employed.

Figure 17:
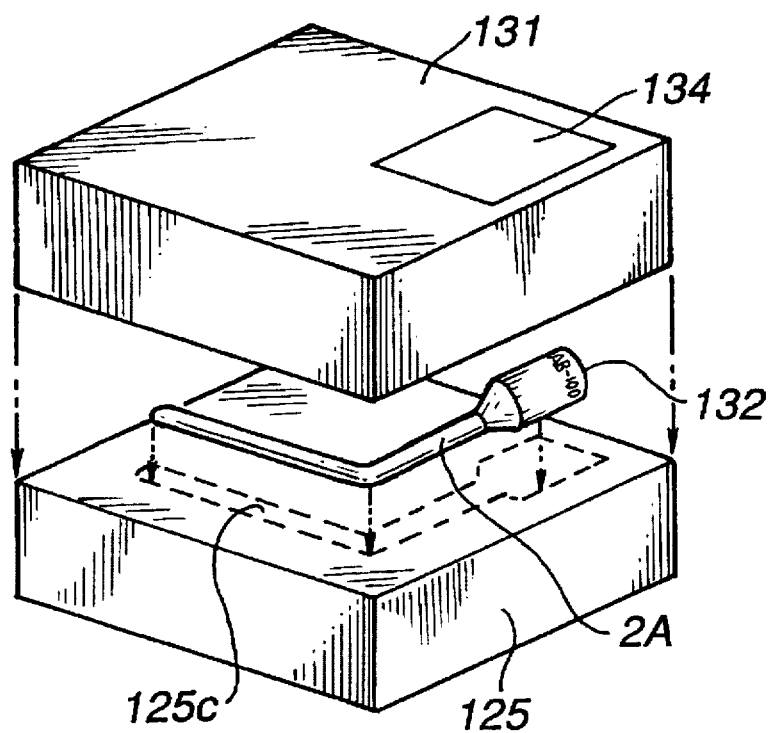
FIG. 17 illustrates a case where a transparent window is formed in a cover for packaging the endoscope cover.
Figure 18:
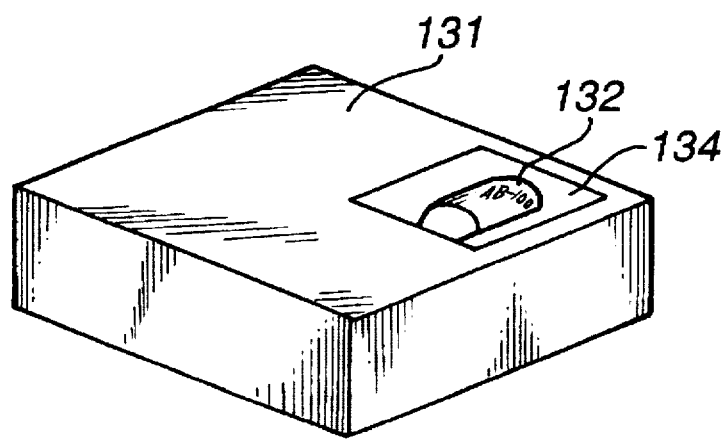
FIG. 18 illustrates a case where the endoscope cover shown in FIG. 17 is packaged.

FIG. 17 illustrates another packaging method of the endoscope cover which is the disposable product wherein the cost is saved. FIG. 18 illustrates a packaged state produced by the packaging method shown in FIG. 17.

As shown in FIGS. 17 and 18, an indication member 132 having the model number or the model name written on the outer surface thereof is provided for the control portion of the endoscope cover 2A to be packaged. The endoscope package 125 for accommodating the endoscope cover 2A has an accommodating chamber 125C formed to correspond to the shape of the endoscope cover 2A, the accommodating chamber 125C accommodating the endoscope cover 2A. Further, a cover 131 of the endoscope package 125 has, on the top surface thereof, a transparent window 134 at a position at which the indication member 132 of the endoscope cover 2A accommodated in the endoscope package 125 can be visually read. The transparent window 134 is made of, for example, a transparent vinyl sheet hermetically applied to the cover 131 of the package.

When the endoscope cover 2A is packaged as shown in FIG. 18 by using the endoscope package 125 and the package cover 131 respectively arranged as described above, the indication member 132 of the model number of the model name of the packaged endoscope cover can be recognized instantaneously. Since the endoscope cover 2A is packaged during sterilization and is maintained in a sterilized state, the problem of the contamination considered to take place due to the use of the transparent window 134 can be overcome because the transparent window 134 is hermetically applied to the package cover 131.

Therefore, this embodiment eliminates the conventional necessity of fastening the indication member 133 of the model number or the model name to the side surface of the package cover 131 to recognize the contents, the model number or the model name of the accommodated article in the form of the package can be recognized. Furthermore, a package form, the cost of which can be reduced, can be realized.

Although this embodiment has the transparent window 134 formed in the top surface of the package cover 131, the transparent window 134 may be extended to the side surface of the endoscope package 125 so that the indications can be recognized from, for example, an upper position or a side position.

The endoscope cover 2A for covering the cover-type endoscope 2B is generally accommodated in a cover package, followed by sterilization and packaging. That is, the sterilized state is maintained by packaging. An example whereby the sterilized state can be recognized instantaneously is shown in FIG. 21.

Figure 21:
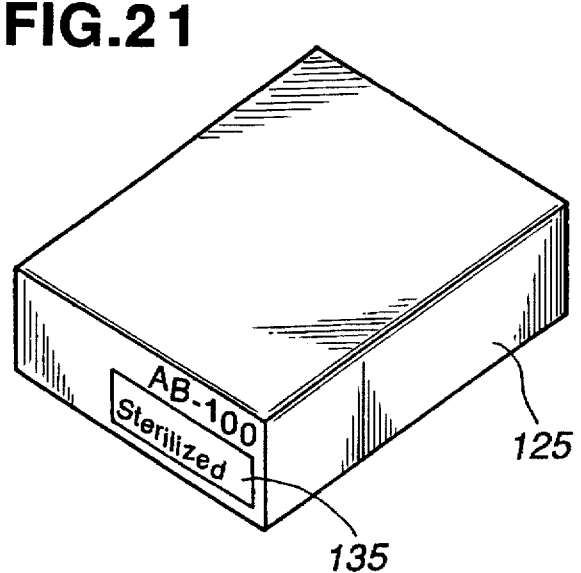
FIG. 21 illustrates a case where an indication portion indicating sterilization has ben completed is provided for the endoscope cover package.

As shown in FIG. 21, a cover package 125 is constituted by a cover and an accommodating portion to be fitted to the cover (omitted from illustration). The accommodating portion accommodates the endoscope cover, followed by sterilization and packaging. This embodiment is characterized in that an indication portion 135 indicating that the accommodated endoscope cover has been sterilized is disposed on the outer surface of the cover package 125, for example, on the front surface of the cover portion of the cover package 125. The indication portion 135 is indicated by, for example, printing, or sealing or the like.

The cover package 125 thus constituted enables a user to instantaneously recognize that the delivered cover package 125 has been sterilized. Since the user (an operator) is able to clearly recognize that the cover package 125 has been sterilized, the act of confirming whether the cover package has been sterilized can be omitted, and, accordingly, it can be quickly used in this inspection.

Although the indication portion 135 according to this embodiment indicates the sterilized state, the unsterilized state may instead be indicated. If the cover package 135 is sterilized by ethylene oxide or by the sterilization method, a seal-type (E, O, gas sterilization confirmation indicator) on the market may be used as the indication portion 135.

Figure 22A:
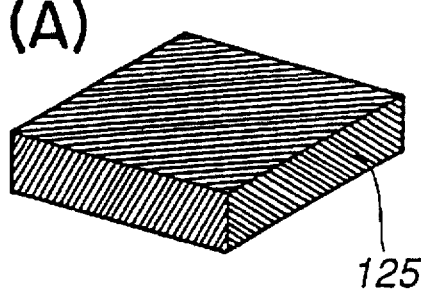
FIG. 22(A)–(D) illustrate a case where the exterior of the endoscope cover package is modified.
Figure 22B:
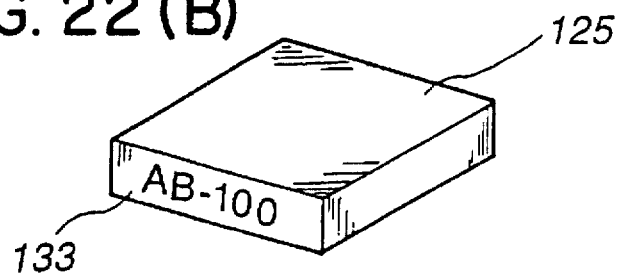
Figure 22C:
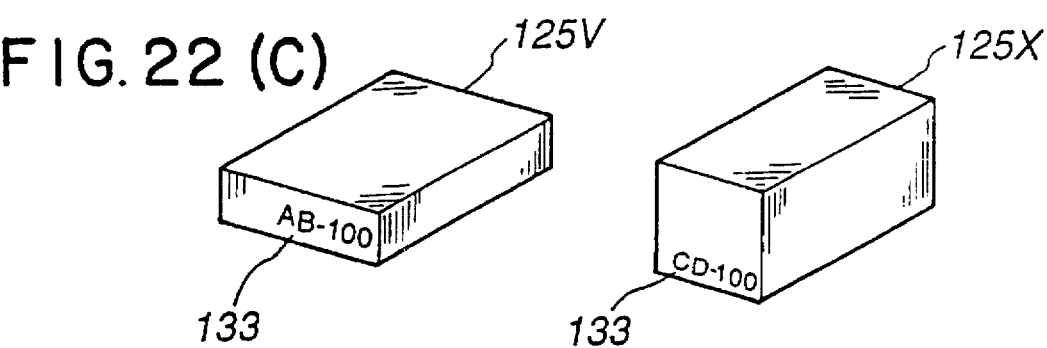
Figure 22D:
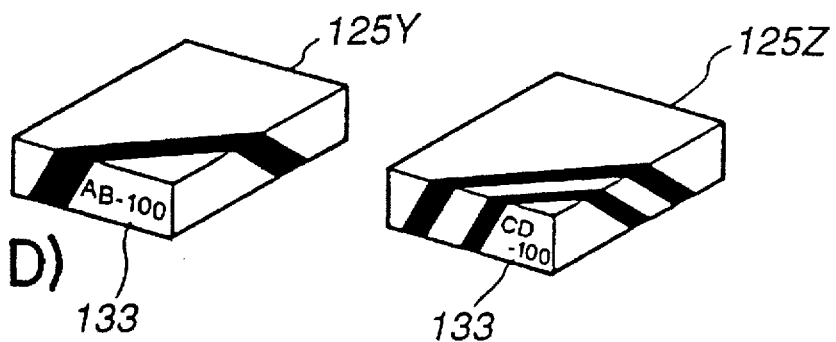

FIG. 22(A)–22(D) illustrate an improvement in the exterior of the cover package. FIG. 22(A) is a perspective view which illustrates a cover package, the color of the exterior of which is changed. FIG. 22(B) is a perspective view which illustrates a cover package, an indication portion is provided on, at least, one side of the exterior. FIG. 22(C) is a perspective view which illustrates a cover package, the shape of which is changed. FIG. 22(D) is a perspective view which illustrates that the design of the exterior is changed.

Since the exterior of the cover package for accommodating the disposable products such as the endoscope cover according to the related art has not been arranged to enable the contents to be recognized, it takes a long time to recognize the contents.

This embodiment is characterized in that at least a portion of the exterior is changed as shown in FIG. 22(A) in order to enable the difference in the contents accommodated in the cover package 125 to be discriminated from the exterior.

For example, a portion of the exterior of the cover package 125 is classified with color to indicate the type of the inspection to be performed with the endoscope cover in such a manner that red indicates the endoscope cover for the upper digestive organs, blue indicates that for the lower digestive organs, yellow indicates that for the duodenum, and green indicates that for the bronchial tube. Furthermore, the model number and the product type are indicated in such a manner that $\phi$2ch is indicated with blue, $\phi$2, 8ch is indicated with yellow and $\phi$3, 2ch is indicated with white.

As shown in FIG. 22(B), this embodiment is also characterized in that at least one side of the exterior of the cover package 125 is provided with an indication portion 133 for indicating the model number or the product type.

The indicating portion 133 is provided for at least one side of the exterior of the cover package 125 by printing or a tape seal so that the contents of the accommodated products can be discriminated from the appearance of the cover package 125.

The indication portion 133 indicates the type of the inspection performed by the endoscope cover such as the upper digestive organs, the lower digestive organs, the duodenum, and the bronchial tube. Furthermore, the model number, such as $\phi$2ch, $\phi$2, 8ch and $\phi$3, 2ch, of the endoscope and the product type, such as AB-100 and CD-100, are indicated.

As a result of the structure described above, the indication portion 133 provided for the cover package 125 enables the type of the endoscope accommodated in the cover package 125 to be instantaneously discriminated. Therefore, a desired endoscope cover can be discriminated even if the endoscope covers are stacked vertically in a narrow storage portion.

FIG. 22(C) illustrates the cover package 125 the shape of which is improved, that is, the size and the shape of the cover package 125 are changed to facilitate the discrimination. Furthermore, the indication portion 133 is provided as shown in FIG. 22(B).

For example, a cover package 125V is constituted by forming the cover package 125 into a rectangular parallelpiped, the height of which is sufficient to accommodate the endoscope cover and by providing the indication portion 133 for at least one side of the exterior. As an alternative to this, a cover package 125X is constituted by forming the cover package 125 into a cube having a length similar to that of the cover package 125V and by providing the indication portion 133 for at least one side of the exterior.

As a result of the structure thus arranged, the shape of the cover package 125 and the contents accommodated in the indication portion 133 can be discriminated instantaneously.

FIG. 22D illustrates a structure comprising the cover package 125, the design of which is changed and the indication portion 133 is provided for at least one side of the exterior.

For example, a cover package 125Y is formed into an elongated shape that connects the front surface, the top surface and the side surface of the exterior of the cover package, so that the discrimination can be made from the three directions. As a result, the discrimination can be made instantaneously even if the cover packages are stacked vertically. As an alternative to this, a cover package 125Z having another indication portion of the foregoing design may be employed.

Therefore, according to this embodiment, the contents accommodated in the cover package 125 can be discriminated instantaneously by simply looking at the outer surface of the cover package 125.

This embodiment may be arranged in such a manner that an indication portion indicating the type and the model number of the endoscope may be provided for the cover packages shown in FIGS. 22(A), 22(B), 22(C) and 22(D).

Figure 23:
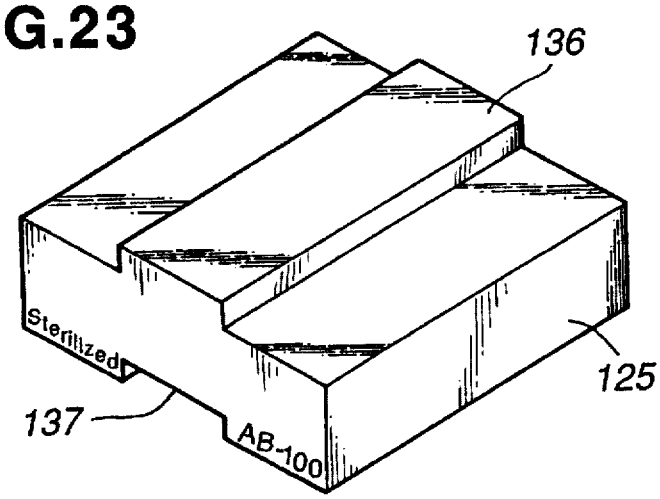
FIG. 23 illustrates a case where a projection and a pit are respectively provided for the two vertical sides of the endoscope cover package.
Figure 24:
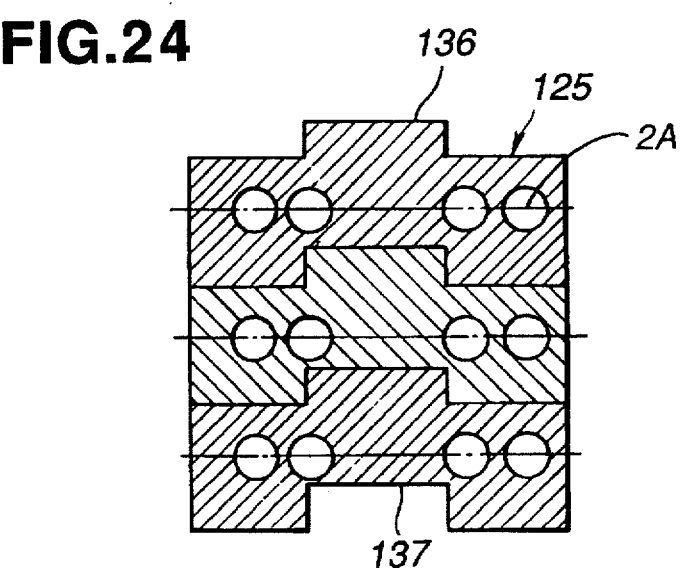
FIG. 24 illustrates a case where a plurality of endoscope cover packages are vertically stacked.

FIG. 23 is a perspective view which illustrates the cover package 125 whereby the space required to store the cover packages 125 shown in FIG. 21 can be reduced. FIG. 24 is a cross-sectional view which illustrates a state where a plurality of the cover packages 125 shown in FIG. 23 are stacked.

As shown in FIG. 23, the cover package 125 has a projection on the top surface thereof and has a recess 137 in the lower surface thereof. In a case where a plurality of the cover packages 125 are stacked vertically as shown in FIG. 24, the foregoing projections 136 and the recesses 137 can be fastened to one another.

If the cover packages are stacked vertically as shown in FIG. 24, the structure thus arranged causes the projection 136 to be fastened to the recess 137 of the upper package 125. As a result, the cover packages 125 are fixed, and, accordingly, load shift can be prevented.

Generally, the disposable products such as the endoscope covers must be stocked and, accordingly, a large quantity of the quantity of the cover packages 125 must be stocked. However, this embodiment enables the cargo shift or the like can be prevented even if they are piled highly. As a result, the small space storage portion can effectively be used. That is, the storage portion can be reduced in size.

Figure 25:
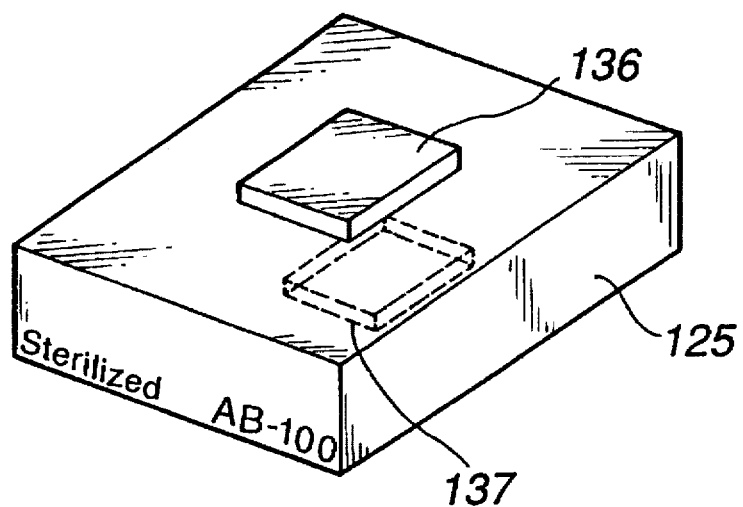
FIG. 25 illustrates a case where the endoscope cover package shown in FIG. 23 is improved and the vertical projection and pit are respectively formed partially.

FIG. 25 illustrates another example of the cover package shown in FIG. 23. FIG. 25 is a perspective view which illustrates the cover package 125 having the projection 136 and the recess 137 in a portion of each of the top surface and the bottom surface thereof.

As shown in FIG. 25, the cover package 125 has the projection 136 in a portion of the top surface thereof, for example, at a position adjacent to the central portion thereof while having the recess 137 in the bottom surface thereof at a position at which the projection 136 can be received by the recess 137.

If a plurality of the cover packages 125 are vertically stacked, the foregoing structure enables the projection 136 to be received by the recess 137 of the upper cover package 125 so that they can be fixed. As a result, the cover packages 125 can be stacked highly even in a narrow storage space.

Therefore, also according to this embodiment, the storage space can be reduced.

The size of the projection 136 and that of the recess 137 according to this embodiment may be determined to be another size if the endoscope cover can be assuredly accommodated, the sterilized state can be maintained and the stacked endoscope covers can be fastened and fixed.

Figure 26:
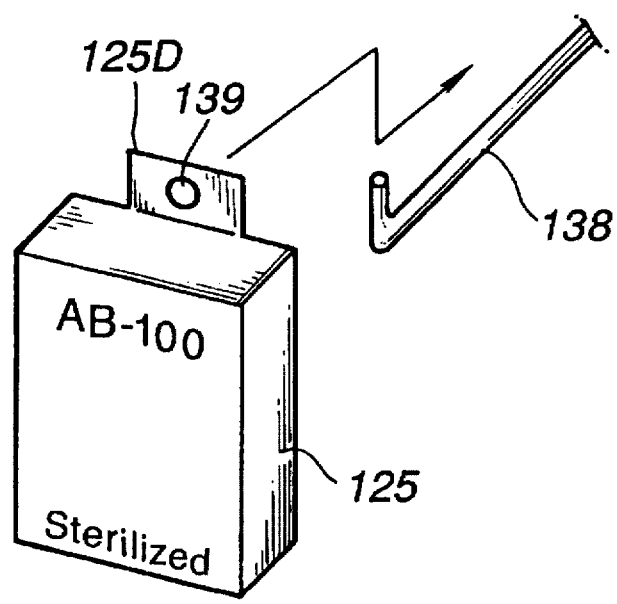
FIG. 26 illustrates a case where the endoscope cover package shown in FIG. 23 is made a suspension type.

FIG. 26 illustrates an example whereby the space required to store the cover packages 125 shown in FIG. 21 can be reduced. FIG. 26 is a perspective view which illustrates a cover package 125 of the suspension type.

As shown in FIG. 26, the cover package 125 has a suspension member 125D extending from the upper portion thereof. Further, the suspension member 125D has, at a position adjacent to the central portion thereof, a suspension hole 139 into which a storage hook member 138 horizontally projecting from, for example, the wall is inserted.

The structure thus arranged enables the cover package 125 to be stored while being suspended in such a manner that the suspension hole 139 formed in the cover package 125 is fastened by the storage hook member 138.

Although it has been difficult to take out the cover package 125 positioned at an upper portion of the stacked cover packages 125 as shown in FIG. 24, this embodiment employing the suspension method enables the desired cover package to be easily taken out. Furthermore, the storage space can be reduced.

Figure 27:
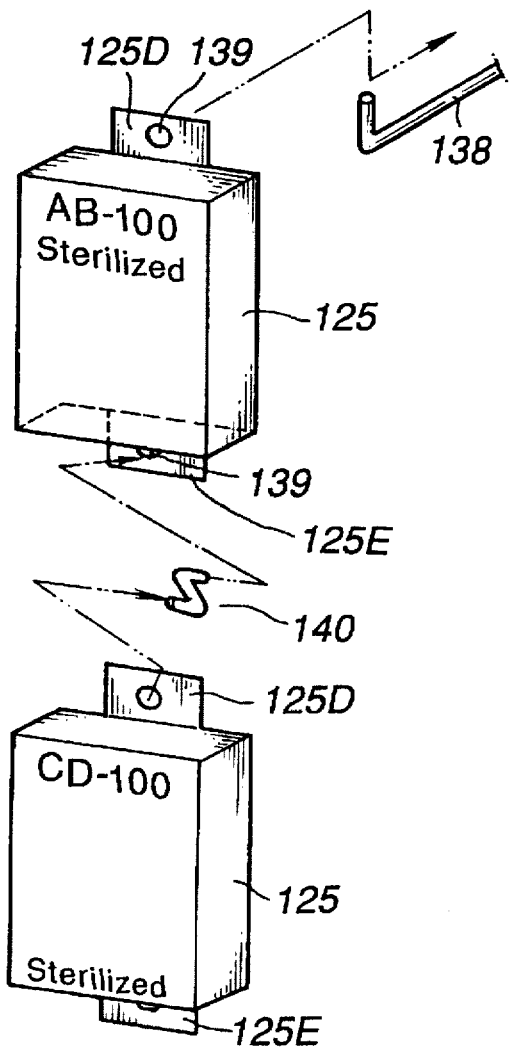
FIG. 27 illustrates a case where the lower portion of the endoscope cover package shown in FIG. 26 is made suspension type.

FIG. 27 illustrates a further improved suspension type cover package 125. This example is characterized in that a suspension member 125E is provided for also the lower portion of the cover package 125.

As shown in FIG. 27, the suspension type cover package 125 shown in FIG. 26 has a suspension member 125E having a size similar to that of the foregoing suspension member 125D. Further, the foregoing suspension member 125E has a suspension hole 139 therein. A suspension member 140 is fastened to the suspension hole 139, and another cover package 125 is suspended from the suspension member 140.

Although a large number of storage hooking members 138 has been required because the number of the cover packages 125 which can be suspended from one storage hooking member 138 has been limited as shown in FIG. 26, the arrangement, in which the suspension members 125D, 125E and suspension member 140 for fastening the suspension members 125D and 125E are provided, enables the cover packages 125 to be vertically suspended. That is, many cover packages 125 can be stored by one storage hooking member. Therefore, the length of the storage hooking member 138 can be shortened and the storage space can be reduced.

Figure 28:
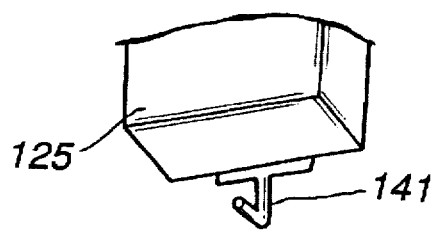
FIG. 28 illustrates a case where the endoscope cover package shown in FIG. 27 is modified and a hook-type suspension portion is provided.

FIG. 28 is a partially broken perspective view which illustrates the cover package 125 characterized in that the suspension member 125E disposed in the lower portion of the cover package 125 shown in FIG. 27 is replaced by a hook-shape suspension portion 141.

As shown in FIG. 28, the suspension portion 141 formed into a hook shape is formed in place of the suspension member 125E disposed in the lower portion of the cover package 125 shown in FIG. 27. The residual elements, the operation and the effect are the same as those of the embodiment shown in FIG. 27, and, therefore, their descriptions are omitted here.

The embodiments shown in FIGS. 26 and 27 may be arranged in such a manner that a cut is partially made in the suspension hole 139 of the suspension member 125D disposed in the upper portion of the cover package 125 so as to take out the cover package 125 with a force which does not bend the storage hooking member 138 if a cover package is positioned in, for example, a deep portion.

Figure 29:
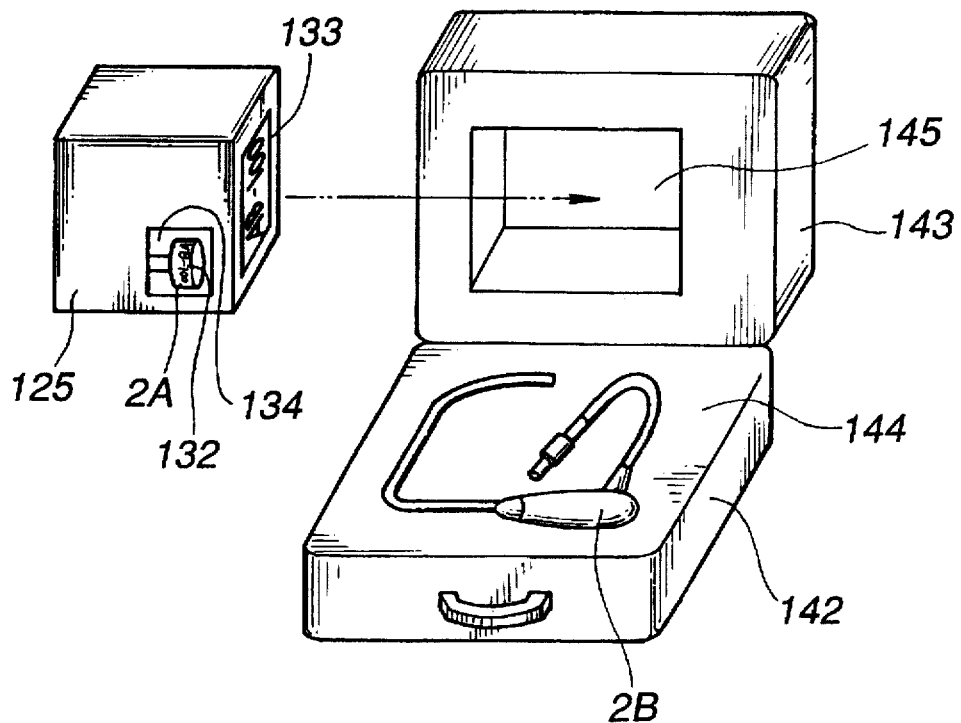
FIG. 29 illustrates a case where a cover package accommodating portion is provided for a cover portion of an endoscope carrying case.

FIG. 29 is a perspective view which illustrates a carrying case of an endoscope capable of carrying both a cover-type endoscope and a cover package accommodating an endoscope cover. As shown in FIG. 29, the endoscope cover 2A is accommodated in the cover package 125 having a transparent window 134 in a portion of the upper surface thereof. The transparent window 134 formed in the cover package 125 enables the indication portion 132 indicating the model number and the model name and provided for the accommodated endoscope cover 2A to be discriminated. Further, the cover package 125 has, on the side surface thereof, the indication portion 133 for indicating the model number and the model name of the accommodated endoscope cover 2A.

On the other hand, the endoscope carrying case 142 for accommodating the cover-type endoscope 2B has an accommodating portion 144 for accommodating the cover-type endoscope 2B. The accommodating portion 144 is made of, for example, resin such as polyurethane formed into a shape adaptable to the cover-type endoscope 2B to be accommodated. As a result, the cover-type endoscope 2B accommodated in the accommodating portion 144 can be protected from breakage due to vibrations or shocks during carriage.

The cover 143 of the endoscope carrying case 142 has a cover package accommodating portion 145 for accommodating the cover package 125 in which the endoscope cover 2A is packaged. The cover package accommodating portion 145 is made of the same material as that of the foregoing endoscope accommodating portion 144 and formed into a shape adaptable to the shape of the cover package 125 to accommodated. As a result, the cover package 125 accommodated in the foregoing cover package accommodating portion 144 can be protected from breakage due to vibrations or shock during the carriage.

Since the endoscope carrying case according to the related art has no accommodating portion for accommodating the cover package, it has been very inconvenient because the cover package and the endoscope carrying case must be carried individually in a case where an inspection with the endoscope is performed at another hospital.

According to this embodiment, the cover-type endoscope 2B and the endoscope cover 2A to be used simultaneously are accommodated in one endoscope carrying case 142. Therefore, they can be carried conveniently in a case where an inspection with the endoscope is performed at another hospital so that the inspection can be performed smoothly. Since the endoscope accommodating portion 144 and the cover package accommodating portion 145 are provided, the cover-type endoscope 2B and the endoscope cover 2A can be protected from breakage from vibrations and shock during the carriage.

This embodiment may be arranged in such a manner that the cover package accommodating portion 145 of the cover 143 of the endoscope carrying case may have a band or the like made of rubber or a magic tape to prevent separation of the accommodated cover package 125 from the cover package accommodating portion 145.

Figure 30:
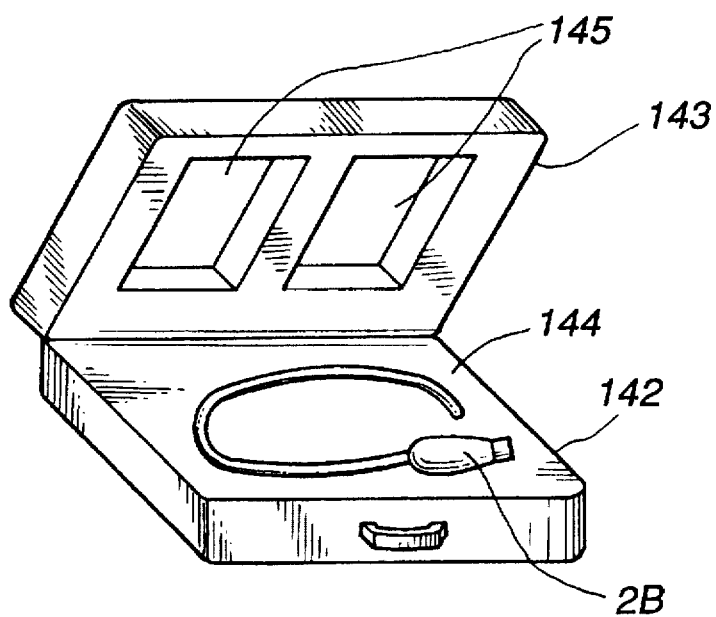
FIG. 30 illustrates a case where another cover package accommodating portion is provided for the endoscope carrying case shown in FIG. 29.

FIG. 30 is a perspective view which illustrates an endoscope carrying case having two cover package accommodating portions shown in FIG. 29.

As shown in FIG. 30, this embodiment has a size resulting from enlarging the size of the endoscope carrying case 142 shown in FIG. 29. Therefore, the cover 143 of the endoscope carrying case has two cover package accommodating portions 145 for accommodating the cover packages 125. As a result, the two cover packages 125 can be accommodated. The other structure and the operations are the same as those of the structure shown in FIG. 29, and, therefore, their descriptions are omitted here.

Therefore, according to this embodiment, the cover-type endoscope 2B and the two endoscope covers 2A can be accommodated in one endoscope carrying case 142. Therefore, the carriage can be conveniently performed even if an inspection with the endoscope is performed at another hospital.

Since two endoscope covers can be simultaneously accommodated, inspections can be performed continuously. Furthermore, the endoscope accommodating portion 144 and the cover package accommodating portion 145 are provided, resulting in that the cover-type endoscope 2B and the endoscope cover 2A can be protected from breakage due to vibrations and shock during the carriage.

Since this embodiment has the arrangement in which the endoscope accommodating portion 144 is also enlarged to be adaptable to the enlarged endoscope carrying case 142, the two cover-type endoscopes 2B may be accommodated in the foregoing endoscope accommodating portion 144. Another accommodating portion for accommodating other disposable products may be provided (a disposable product such as a control-portion cover or a disposable mouth piece which is used in each inspection) in addition to the foregoing endoscope accommodating portion 144.

This embodiment may be arranged in such a manner that the endoscope carrying case 142 may accommodate a plurality of the cover-type endoscopes 2B and a plurality of the endoscope covers 2A. The endoscope carrying case 142 may be formed to have the size capable of accommodating the foregoing elements.

Figure 31:
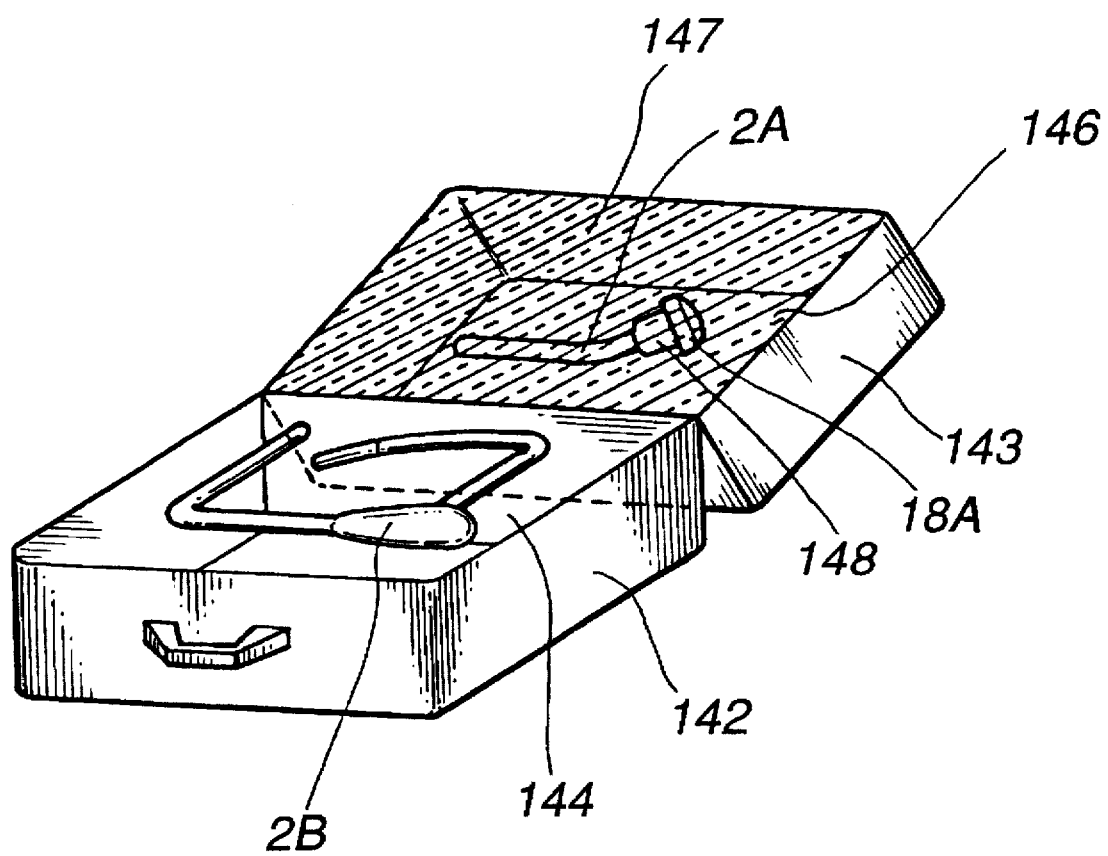
FIG. 31 illustrates a case where a tray is provided for the cover portion of the endoscope carrying case followed by sealing.

FIG. 31 is a perspective view which illustrates an endoscope carrying case arranged in such a manner that the cover of the endoscope carrying case is formed into a tray which accommodates the endoscope cover.

As shown in FIG. 31, the endoscope carrying case 142 has an arrangement that the cover 143 of the endoscope carrying case 142 is formed into a tray 146 which accommodates the endoscope cover 2A. The accommodated endoscope cover 2A is supported by a holder 148 provided for the tray 146. The holder 148 is made of a pipe or the like formed into, for example, a cylindrical shape, the holder 148 being fastened in such a manner that its outer surface projects over the bottom surface of the tray in a diagonal state. When the endoscope cover 2A is accommodated in the tray 146, the insertion portion of the endoscope cover 2A, that is, the leading portion is first inserted into the holder 148. Thus, the endoscope cover 2A is held in a state where it is hooked by the flange portion 18A provided for the end portion of the endoscope cover 2A.

Furthermore, the endoscope cover 2A is accommodated, it is sterilized, and a sealing sheet 147 for covering the tray 146 is applied to maintain the sterilized state. The sealing sheet 147 is made of, for example, a vinyl material applied to the tray 146, that is, to the overall end portion of the cover 143 of the endoscope carrying case. As a result, the sterilized state of the tray 146 can be maintained. When the endoscope cover 2A is used, the sealing sheet 147 must be broken so that the preparation for performing an inspection can be made easily.

Since the accommodating portion 144 of the cover-type endoscope is arranged similarly to that shown in FIG. 29, its description is omitted here.

Therefore, according to this embodiment, the tray 143 having the holding portion 148 is provided for the cover 143 of the endoscope carrying case 142, and the sealing sheet 147 for maintaining the sterilized state is used. As a result, the cover package 125 for packaging the endoscope 2A can be omitted. Since the cover-type endoscope 2B and the endoscope cover 2A can be carried simultaneously by one endoscope carrying case 142, the carriage can be performed conveniently.

This endoscope may be arranged in such a manner that the holder 148 is integrally formed with the tray 146. If it is able to securely hold the endoscope cover 2A, another structure may be employed.

Although the invention has been described in its preferred form with a certain degree of particularly, it is understood that the present disclosure of the preferred form has been changed in the details of construction and the combination and arrangement of parts may be resorted to without departing from the spirit and the scope of the invention as hereinafter claimed.

What is claimed is:

1. An endoscope system including an endoscope cover apparatus and an endoscope cover expanding apparatus comprising:

a joint portion for detachably mounting a control portion of a cover-type endoscope passing therein;

an endoscope insertion channel into which said endoscope is inserted; and a connection tubular passage connectable to said endoscope cover expander, said connection tubular passage being integrally formed with said joint portion so as not to be detachable and which is connected to said endoscope insertion channel, wherein said connection tubular passage is divided into a first portion adjacent to said joint portion and a second portion adjacent to said endoscope cover expander and, wherein said connection tubular passage has an endoscope cover holding device capable of connecting said first portion of said connection tubular passage adjacent to said joint portion and said second portion of said connection tubular passage adjacent to said endoscope cover expander.

2. An endoscope cover apparatus into which a cover-type endoscope is inserted so as to be covered therewith, comprising:

a joint portion which is provided with a passage and a channel therein and to which a control portion of a cover-type endoscope is detachably connected whenever said cover-type endoscope is passed through said channel, said joint portion further having at least one branching portion provided in at least either one of said passage and said channel so as to be opened toward the outside;

an insertion-portion cover which is formed into an elongated shape and having one end connected to said joint portion;

a cover end portion which is connected to the other end of said insertion-portion cover;

an endoscope insertion channel which is provided within said insertion-portion cover and said cover end portion and which communicates with said channel provided within said joint portion;

a first tubular passage member which is provided within said insertion-portion cover and entirely outside said endoscope and which is in fluid communication with said passage within said joint portion at one end thereof and also is in fluid communication with an opening within said cover end portion at the other end thereof, said first tubular passage member being connected to said passage within said joint portion without passing through said endoscope at a location which is at the leading edge of said branching portion provided in said passage within said joint portion; and a second tubular passage member which is in fluid communication with said passage within said joint portion at one end thereof and the other end of which is connected to an external device, said second tubular passage member being connected to said passage within said joint portion at a location which is at the proximal side of said branching portion provided in said passage within said joint portion.

3. An endoscope cover apparatus according to claim 2, wherein said passage in said joint portion is a suction passage.

4. An endoscope cover apparatus according to claim 3, wherein a branching portion is provided in said passage as the suction passage formed within said joint portion, said branching portion being opened toward the outside so that a forceps or a curing tool may be inserted therefrom.

5. An endoscope cover apparatus according to claim 2, wherein said passage in said joint portion is one of an air supply passage and a water supply passage.

6. An endoscope cover apparatus according to claim 2, wherein a plurality of said passages are provided within said joint portion, and each of said passages is one of a suction passage, an air supply passage and a water supply passage.

7. An endoscope cover apparatus according to claim 2, wherein said first tubular passage member consists of a multilumen tube.

8. An endoscope cover apparatus according to claim 2, wherein said second tubular passage member consists of a multilumen tube.

9. An endoscope cover apparatus according to claim 2, wherein said cover end portion consists of a multilumen tube.

10. An endoscope cover apparatus according to claim 2, wherein said joint portion consists of a multilumen tube.

11. An endoscope cover apparatus according to claim 2, wherein a plurality of fluid-passages are formed in said first tubular passage member, in said joint portion and in said second tubular passage member, respectively, all of which communicate with one another.

12. An endoscope cover apparatus according to claim 11, said plurality of fluid-passages are formed in a multilumen tube.

13. An endoscope cover apparatus according to claim 2, wherein an expansion passage communicates with an opening of said branching portion provided in said channel within said joint portion.

14. An endoscope cover apparatus into which a cover-type endoscope is inserted so as to be covered herewith, comprising:

a joint portion which is provided with a passage and a channel therein and to which a control portion of a cover-type endoscope is detachably connected whenever said cover-type endoscope is passed through said channel;

an insertion-portion cover which is formed into an elongated shape having one end connected to said joint portion;

a cover end portion connected to the other end of said insertion-portion cover;

an endoscope insertion channel which is provided within said insertion-portion cover and said cover end portion and which communicates with said channel provided within said joint portion;

a first tubular passage member which is provided within said insertion-portion cover and entirely outside said endoscope and which is in fluid communication with said passage within said joint portion at the other end thereof;

a second tubular passage member which is in fluid communication with said passage within said joint portion at one end thereof and the other end of which is connected to an external device;

an expansion tubular passage provided within said joint portion and which communicates with said endoscope insertion channel;

a tubular passage member which passage communicates with said expansion tubular passage and which can be connected to an endoscope cover expander serving as an external device.

* * * * *